(12) United States Patent
Wixted

(10) Patent No.: US 11,571,243 B2
(45) Date of Patent: Feb. 7, 2023

(54) EXTERNAL FIXATION CLAMP AND SYSTEMS FOR MEDICAL PROCEDURES

(71) Applicant: Beth Israel Deaconess Medical Center, Inc., Boston, MA (US)

(72) Inventor: John Wixted, Northborough, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 388 days.

(21) Appl. No.: 16/415,791

(22) Filed: May 17, 2019

(65) Prior Publication Data
US 2019/0350623 A1  Nov. 21, 2019

Related U.S. Application Data

(60) Provisional application No. 62/673,601, filed on May 18, 2018.

(51) Int. Cl.
*A61B 17/64* (2006.01)
*A61B 17/00* (2006.01)
*A61B 17/56* (2006.01)

(52) U.S. Cl.
CPC ...... *A61B 17/6458* (2013.01); *A61B 17/6441* (2013.01); *A61B 2017/00526* (2013.01); *A61B 2017/564* (2013.01)

(58) Field of Classification Search
CPC .............................. A61B 17/64–6491
See application file for complete search history.

(56) References Cited

U.S. PATENT DOCUMENTS

| | | | |
|---|---|---|---|
| 3,736,629 A | 6/1973 | Blake | |
| 4,620,533 A | 11/1986 | Mears | |
| D305,608 S | 1/1990 | Hahn | |
| 5,741,252 A | 4/1998 | Mazzio et al. | |
| 5,921,985 A | 7/1999 | Ross, Jr. et al. | |

(Continued)

FOREIGN PATENT DOCUMENTS

| | | |
|---|---|---|
| CH | 657899 A5 | 9/1986 |
| EP | 0883380 B1 | 8/2001 |

(Continued)

OTHER PUBLICATIONS

International Search Report and Written Opinion issued for corresponding PCT International Patent No. PCT/US/2019/032962 dated Aug. 20, 2019.

(Continued)

*Primary Examiner* — Nicholas J Plionis
(74) *Attorney, Agent, or Firm* — McCarter & English, LLP

(57) ABSTRACT

The present invention relates to an external fixation system including at least one pair of connected clamp units forming at least one clamp. Each of the clamp units includes: a first component comprising a molded metal, the first component having a first exterior surface having a plurality of voids formed therein to define a plurality of interconnected ribs and a first periphery having at least one first pin groove formed therein; and a second component mated to the first component and including a second periphery having at least one second pin groove formed therein, the at least one first pin groove and at least one second pin groove together forming a fixation pin holder. A fixation pin is held in at least one of the fixation pin holders.

39 Claims, 22 Drawing Sheets

(56) References Cited

U.S. PATENT DOCUMENTS

| | | |
|---|---|---|
| 5,976,133 A | 11/1999 | Kraus et al. |
| 6,059,784 A | 5/2000 | Perusek |
| 6,080,153 A | 6/2000 | Mata et al. |
| 6,277,069 B1 | 8/2001 | Gray |
| D448,280 S | 9/2001 | Bourgerie |
| 6,565,564 B2 | 5/2003 | Hoffman et al. |
| 7,048,735 B2 | 5/2006 | Ferrante et al. |
| 7,261,713 B2 | 8/2007 | Langmaid et al. |
| 7,491,008 B2 | 2/2009 | Thomke et al. |
| 7,762,308 B2 | 7/2010 | Crawford et al. |
| 7,801,613 B2 | 9/2010 | Li et al. |
| 7,806,623 B2 | 10/2010 | Thomke et al. |
| 7,875,030 B2 | 1/2011 | Hoffmann-Clair et al. |
| D663,030 S | 7/2012 | Murner et al. |
| D679,013 S | 3/2013 | Green et al. |
| D682,426 S | 5/2013 | Dominik et al. |
| 8,444,643 B2 | 5/2013 | Thomke et al. |
| 8,808,289 B2 | 8/2014 | Busch et al. |
| 8,821,491 B2 | 9/2014 | Chreene et al. |
| D714,629 S | 10/2014 | Irgens |
| 8,992,579 B1 | 3/2015 | Gustine et al. |
| 9,155,561 B2 | 10/2015 | Chang |
| 9,757,573 B2 | 9/2017 | Glynn et al. |
| 9,883,890 B2 | 2/2018 | Miller et al. |
| D836,184 S | 12/2018 | Lippka |
| D859,136 S | 9/2019 | Tenander et al. |
| D859,137 S | 9/2019 | Tenander et al. |
| D859,970 S | 9/2019 | Tenander et al. |
| D859,971 S | 9/2019 | Tenander et al. |
| D865,507 S | 11/2019 | Tenander et al. |
| 10,702,308 B2 | 7/2020 | Mullaney |
| 10,945,765 B2 | 3/2021 | Miller |
| D926,019 S | 7/2021 | Orikawa |
| 2001/0051806 A1 | 12/2001 | Ballier |
| 2003/0187432 A1 | 10/2003 | Johnson et al. |
| 2006/0052781 A1 | 3/2006 | Thomke et al. |
| 2006/0177263 A1 | 8/2006 | Thomke et al. |
| 2007/0178005 A1 | 8/2007 | Broadley et al. |
| 2009/0198235 A1 | 8/2009 | Steiner et al. |
| 2009/0306661 A1 | 12/2009 | Thomke et al. |
| 2010/0298827 A1* | 11/2010 | Cremer ............... F16B 7/0493 606/54 |
| 2012/0089142 A1* | 4/2012 | Mullaney ........... A61B 17/6466 606/54 |
| 2013/0226179 A1* | 8/2013 | Chreene ............ A61B 17/6466 606/54 |
| 2016/0303357 A1 | 10/2016 | Simon, Jr. et al. |
| 2016/0310167 A1* | 10/2016 | Tepic ................... A61B 17/645 |
| 2016/0199098 A1 | 11/2016 | Slagle |
| 2017/0071633 A1* | 3/2017 | Sanders ............. A61B 17/6466 |
| 2017/0281236 A1 | 10/2017 | Mussolin |
| 2017/0303968 A1* | 10/2017 | Kao ..................... A61B 17/848 |

FOREIGN PATENT DOCUMENTS

| | | |
|---|---|---|
| RU | 2521839 C1 | 7/2014 |
| WO | 2009/042836 A1 | 4/2009 |

OTHER PUBLICATIONS

Beth Israel Deaconess Medical Center, Equipment Listing. Retrieved online at: https://www.bidmc.org/research/core-facilities/animal-metabolic-physiology-core/equipment-listing. 4 pages, (2021).

* cited by examiner

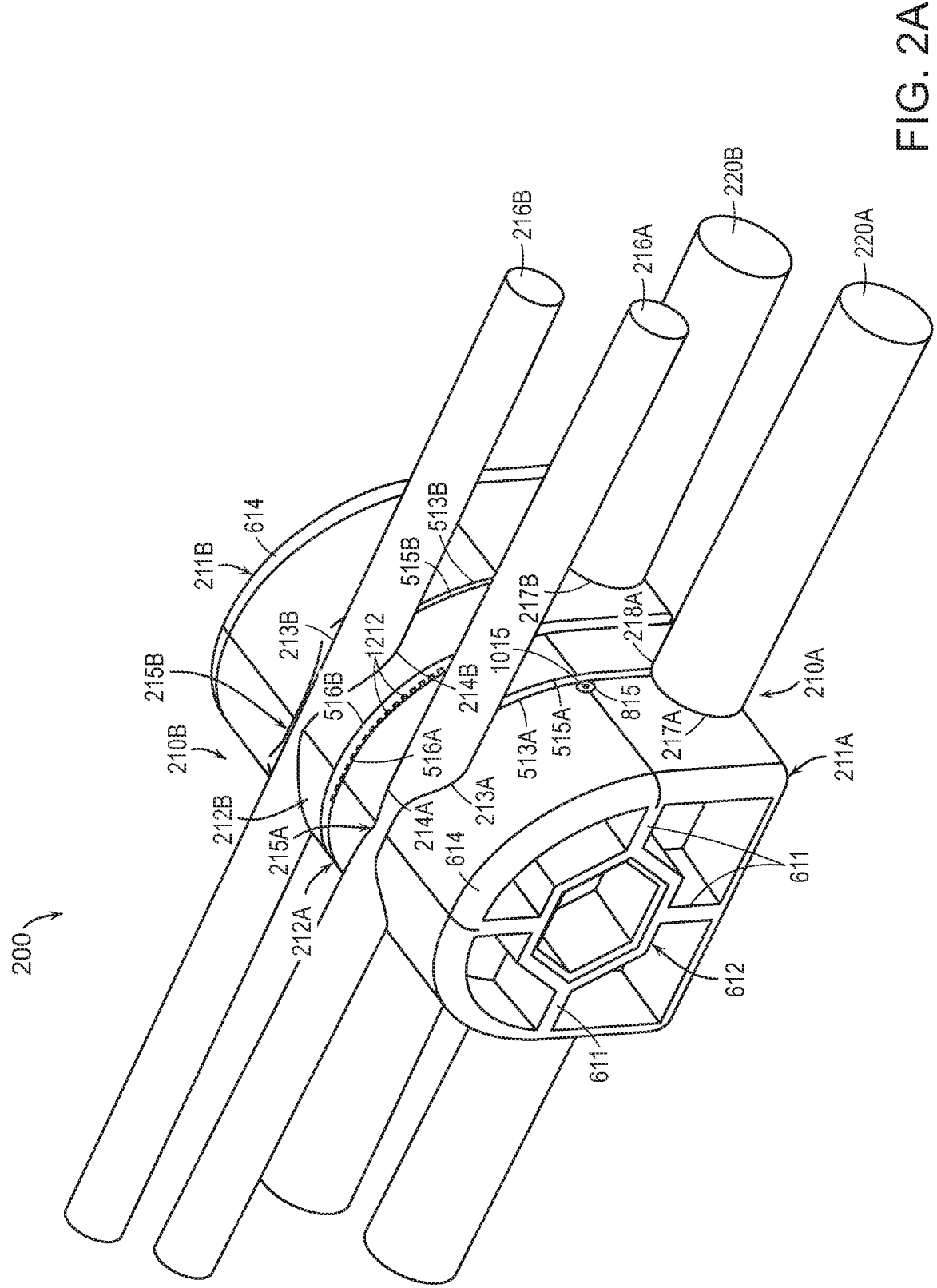

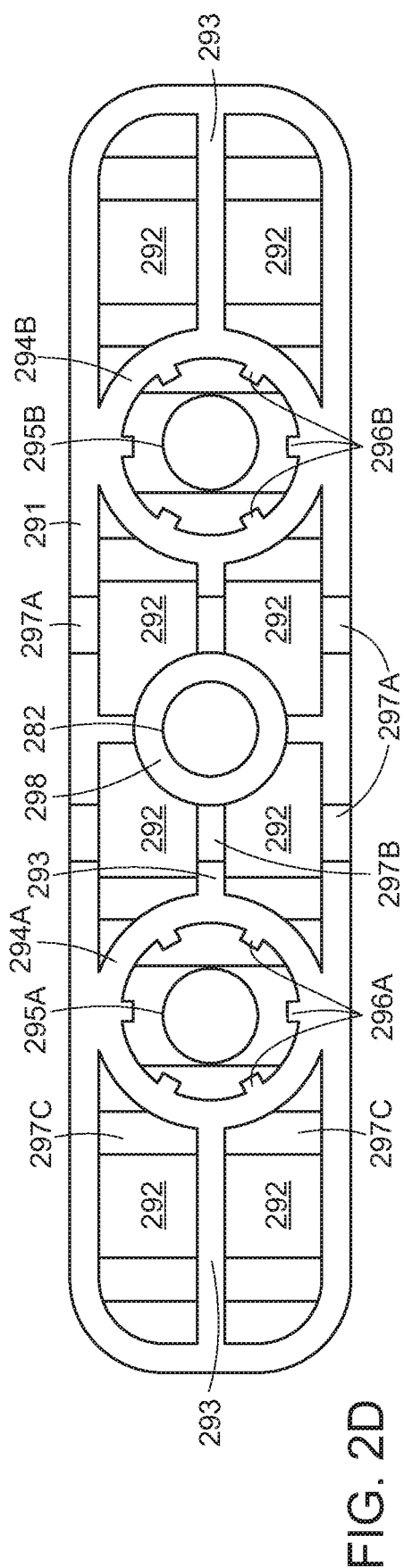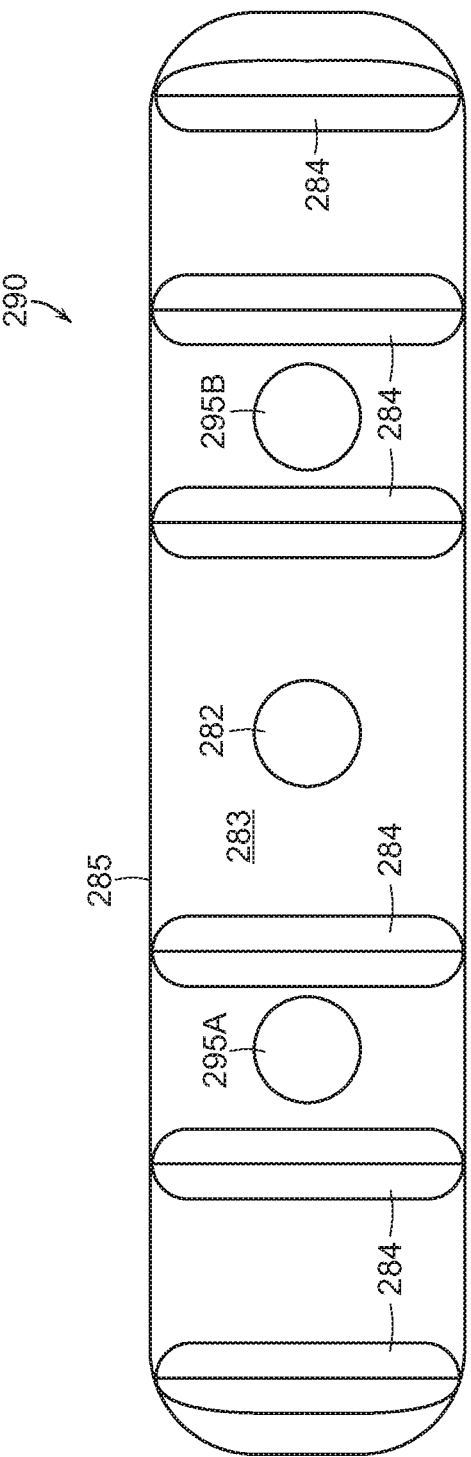

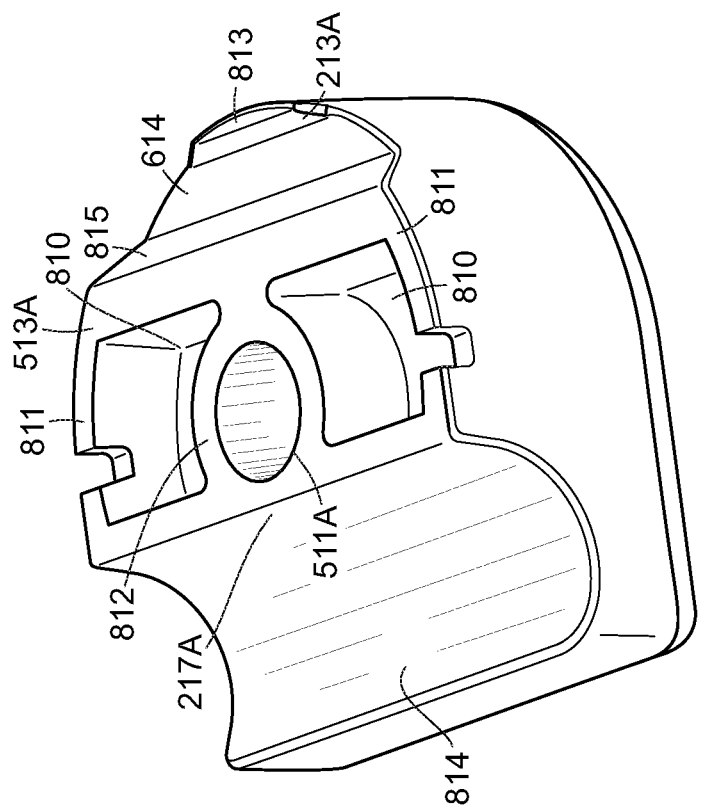
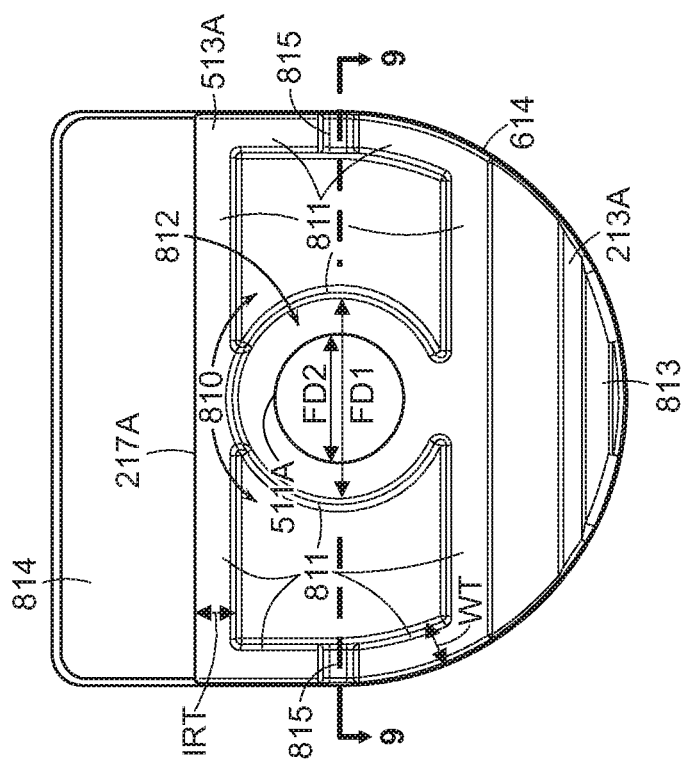
FIG. 8B
FIG. 8A

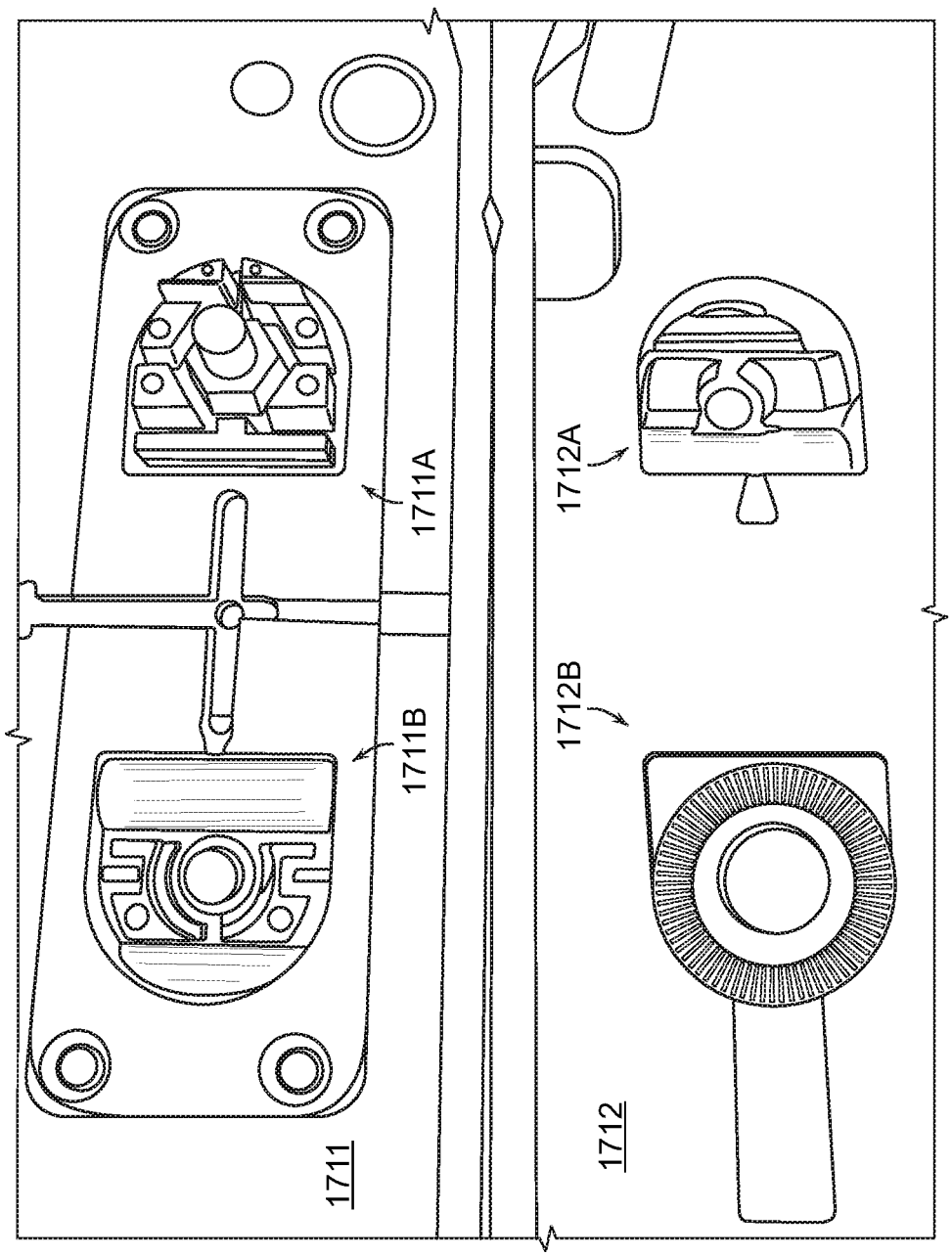

EXTERNAL FIXATION CLAMP AND SYSTEMS FOR MEDICAL PROCEDURES

This application claims priority to U.S. Provisional Application No. 62/673,601, filed May 18, 2018, and is related to U.S. Design application Ser. No. 29/691,690, filed May 17, 2019 by John Wixted and having the title EXTERNAL FIXATION CLAMP FOR MEDICAL PROCEDURES, these applications being incorporated herein by reference in their entireties.

BACKGROUND OF THE INVENTION

An external fixation system is often used for stabilizing the human skeleton after injury. Pins or wires can be affixed to various bones using minimal incisions, and clamps and connecting elements, such as bars, can be used to connect the pins or wires together. Such a system can provide a quick, safe, and effective way to stabilize the skeleton using elements that mostly reside outside of the body. In some instances, fractured bones can be temporarily stabilized prior to more extensive surgery. This can be beneficial by allowing the skin and soft tissues to recover from an initial traumatic injury prior to more extensive surgery. In other instances, the external fixators themselves can be used for definitively stabilizing broken bones, which can then heal with appropriate alignment after stabilization. Other common uses include the stabilization of joints, such as the knee or the elbow, where injuries to ligamentous structures cause instability, which can be treated by applying an external fixation device.

Generally, an external fixator typically uses certain common elements. Specifically, two or more connectors are fixed to either the same or different bones, and these connectors are then secured to each other by a clamping system. The connectors, which are affixed to the bones, may themselves be thin wires placed under tension or more substantial screw-type pins. Clamping systems may vary as well, in that some clamping systems include bars and clamps in a primarily linear configuration, and some make use of bars and clamps in a circular, ring-type configuration for connecting those elements, which are affixed to the bone. In less common configurations, the bars, which work as connection members, can themselves have mechanisms to adjust their length or position within the frame system. Nonetheless, the concept of connecting the pins by a clamping system with connecting members is typically used in external fixators. Prior art metal clamps are fabricated by computer controlled machine tools and thus are expensive to fabricate.

To maintain suitable stability after application of an external fixator, two conditions must be met. First, the interface between the connector and the bone, referred to as the bone-pin interface, needs to remain stable. Should the pin become situated in infected tissue or bone, for example, the frame construct may lose stability as the pin or wire can loosen within the bone. Second, the external fixation system of clamps and connecting members must connect the pins with sufficient rigidity to ensure that bones being stabilized do not lose their relative position. In this sense, the clamping elements become crucial to the overall rigidity and performance of the external fixation system.

However, further improvements of external fixation devices are needed to improve the effectiveness and availability of treatment.

SUMMARY OF THE INVENTION

The present invention relates to an external fixation system including one or more clamps that comprise molded metal elements with interconnected ribs to provide an improved and efficient method for fixating bones wherein the metal elements have the strength and rigidity required.

In some exemplary embodiments disclosed herein, an external fixation system includes at least one pair of connected clamp units forming at least one clamp. Each of the clamp units includes: a first component comprising a molded metal, the first component having a first exterior surface having a plurality of voids formed therein to define a plurality of interconnected ribs and a first periphery having at least one first pin groove formed therein; and a second component mated to the first component and including a second periphery having at least one second pin groove formed therein, the at least one first pin groove and at least one second pin groove together forming a fixation pin holder. A fixation pin is held in at least one of the fixation pin holders. Note that pins, bars, rods, and wires, referred to generally herein as "connector elements" or "fixation elements," serve to couple the clamp(s) to other system elements or the bones, joint elements, or tissue of a patient. The clamps operate to frictionally engage the connector elements to retain rigid alignment of orthopedic members of the patient to promote healing of bone.

In some exemplary embodiments disclosed herein, an orthopaedic clamp includes a first component comprising a molded metal, the first component having a first exterior surface having a plurality of voids formed therein to define a plurality of interconnected ribs, a first opening extending through the first exterior surface to a first interior surface opposite the first exterior surface, and a first periphery having at least one first pin groove formed therein.

In some exemplary embodiments disclosed herein, a method of forming a clamp component includes: filling a mold with a metallic powder comprising metal granules, the mold having a plurality of void projections and at least one pin groove projection; and, under selected conditions of temperature and pressure, fusing the metal granules together in the mold to form the clamp component, the clamp component having a first exterior surface having a plurality of voids corresponding to the plurality of void projections formed therein to define a plurality of interconnected ribs and a first periphery having at least one first pin groove corresponding to the at least one pin groove projection formed therein.

The clamps components can be assembled and connected together by bars having diameters in a range of 8-11 mm. The bars can be used in combination with molded metal components that are temporarily or permanently placed in the patient to connect bones of the patient. Bones associated with the arm, knee, leg, ankle, hip and shoulder can be treated using the devices and methods described herein.

BRIEF DESCRIPTION OF THE DRAWINGS

Other features and advantages of the present invention will be apparent from the following detailed description of the invention, taken in conjunction with the accompanying drawings of which:

FIG. 2A is a perspective view of an exemplary embodiment of a clamp shown in FIG. 1 including a pair of connected clamp components;

FIG. 2D is a top view of the exterior surface shown in FIG. 2C;

FIG. 2E is a top view of an interior surface of one of the clamp components illustrated in FIG. 2B;

FIG. 8A is a top view of an interior surface of the first clamp component shown in FIGS. 6A-7;

FIG. 8B is a perspective view of the interior surface of the first clamp component shown in FIGS. 6A-7;

FIG. 17B is a top view of a mold for creating first and second clamp components.

DETAILED DESCRIPTION OF THE INVENTION

Figure 1:
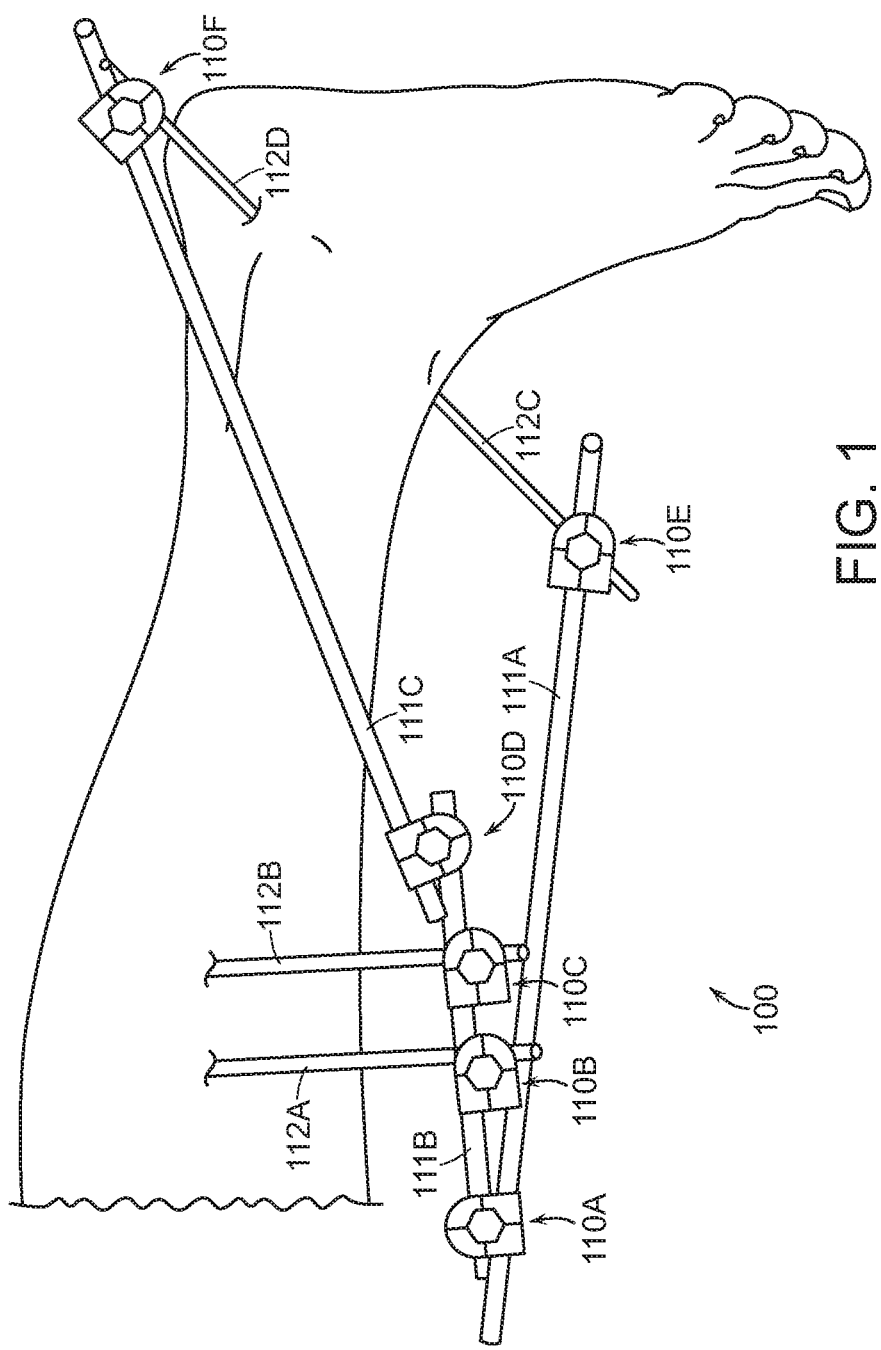
FIG. 1 is a perspective view of an exemplary embodiment of an external fixation system stabilizing bones in the tibia and foot of a subject.

Referring now to the drawings, and more particularly to FIG. 1, an exemplary embodiment of an external fixation system 100 is shown that includes one or more clamps 110A, 110B, 110C, 110D, 110E, 110F that stabilize one or more bones of a subject, which may be located in the foot and tibia, for example. While the external fixation system 100 is shown connected to bones of the subject that are in the foot and tibia, it should be appreciated that the external fixation system 100 may be used to stabilize bones in other locations, such as the arm, wrist, hip, or femur. Some of the clamps, such as clamps 110A and 110D, may be interconnecting clamps that interconnect fixation clamps, such as clamps 110B, 110C, 110E, and 110F, to one another via connecting bars or rods 111A, 111B, 111C in order to maintain the fixation clamps 110B, 110C, 110E, 110F in fixed positions relative to one another and stabilize the bone(s). The fixation clamps 110B, 110C, 110E, 110F, can connect to one or more bones of the subject via fixation pins 112A, 112B, 112C, 112D to form a bone-pin interface. In some embodiments, fixation wires may be used instead of, or in addition to, fixation pins. The pins 112A, 112B, 112C, 112D and bars 111A, 111B, 111C are generally linear, rigid connector elements. Fixation wires can be flexible connector elements that are longitudinally rigid but can bend to accommodate additional fixation geometries. It should thus be appreciated that the clamps 110A, 110B, 110C, 110D, 110E, 110F work in conjunction to stabilize the bones of the subject, even if all of the clamps are not directly connected to bone.

Referring now to FIGS. 2A and 3-5, an exemplary embodiment of a clamp 200 is shown that includes a pair of clamp units, such as a first clamp unit 210A and a second clamp unit 210B, connected to one another to form the clamp 200. It should be appreciated that the clamps 110A, 110B, 110C, 110D, 110E, 110F shown in FIG. 1 can have a similar or identical structure to the clamp 200 shown in FIGS. 2A and 3-5. As can be seen, each of the clamp units 210A, 210B can have a respective first component 211A, 211B mated with a respective second component 212A, 212B, with the two second components 212A, 212B abutting against one another. Each first component 211A, 211B includes a corresponding first pin groove 213A, 213B and each second component 212A, 212B includes a corresponding second pin groove 214A, 214B. The first pin groove 213A and second pin groove 214A of the first clamp unit 210A together form a fixation pin holder 215A and the first pin groove 213B and second pin groove 214B of the second clamp unit 210B together form a fixation pin holder 215B, with each of the fixation pin holders 215A, 215B holding a respective fixation pin 216A, 216B, which can connect to a bone of a subject. Similarly, each first component 211A, 211B can include a first bar groove 217A, 217B and each second component 212A, 212B can include a second bar groove 218A, 218B. The first bar groove 217A and second bar groove 218A of the first clamp unit 210A together form a bar holder 219A and the first bar groove 217B and second bar groove 218B of the second clamp unit 210B together form a bar holder 219B, with each of the bar holders 219A, 219B holding a respective connecting bar 220A, 220B, which can connect the clamp units 210A, 210B, and therefore the clamp 200, to other clamps in the external fixation system 200. Thus, the clamp 200 can connect to one or more bones of a subject as well as other clamps, which may also be connected to one or more bones of a subject, to form an external fixation system.

Figure 5:
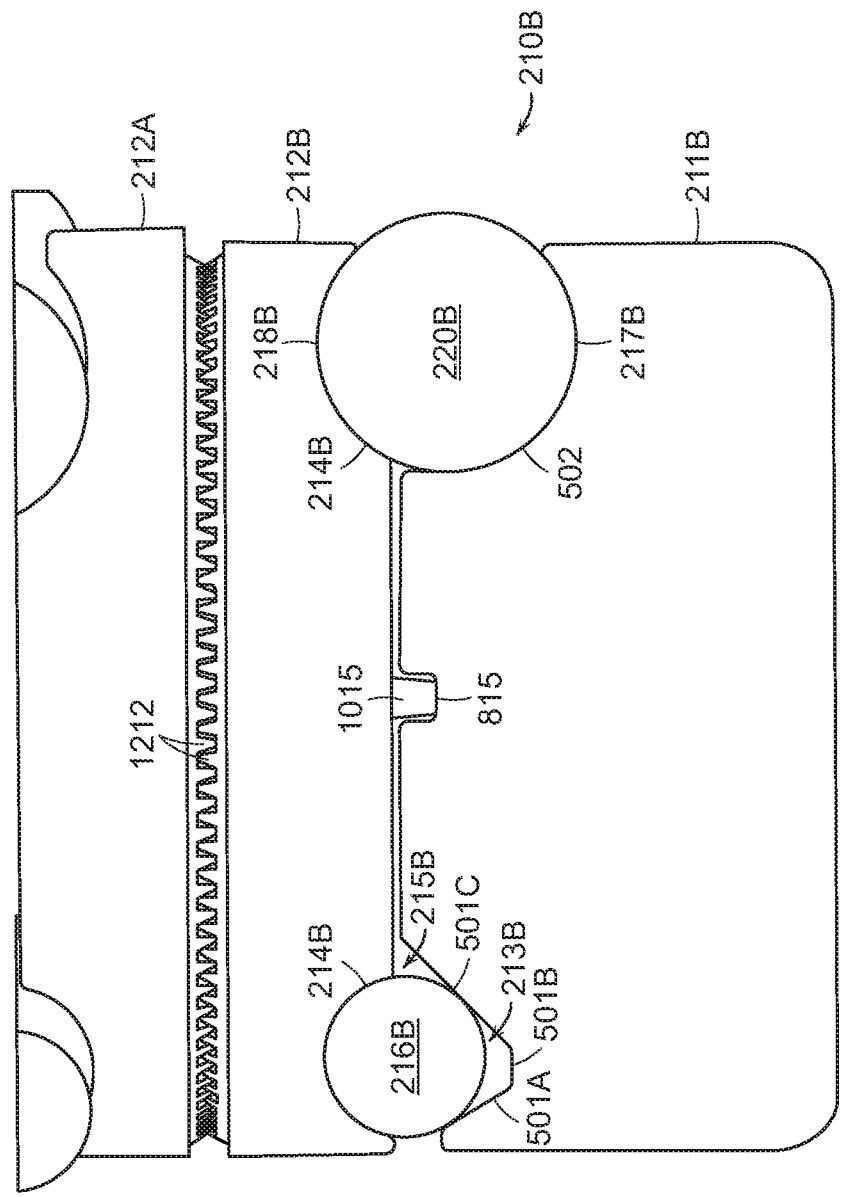
FIG. 5 is a close-up perspective view of the clamp shown in FIGS. 2A and 3-4.

As can be seen in FIG. 5, the first pin groove 213B of the second clamp unit 210B may be formed as a plurality of linear surfaces 501A, 501B, 501C while the second pin groove 214B may be formed as a substantially curved surface 502 that generally conforms to the round shape of the fixation pin 216B held in the fixation pin holder 215B. It should be appreciated that the shapes of the respective pin grooves 213B, 214B are exemplary only, and each of the pin grooves 213B, 214B may be formed to have any suitable shape for holding the fixation pin 216B in the fixation pin holder 215B. In some embodiments, the first pin groove 213A and second pin groove 214A forming the fixation pin holder 215A of the first clamp unit 210A have an identical shape to the pin grooves 213B, 214B of the second clamp unit 210B. The first bar groove 217B and the second bar groove 218B forming the bar holder 219B of the second clamp unit 210B may each have a substantially round shape generally corresponding to the shape of the connecting bar 220B held in the bar holder 219B. In some embodiments, the first bar groove 217A and the second bar groove 218A forming the bar holder 219A of the first clamp unit 210A may have an identical shape to the bar grooves 217B, 218B of the second clamp unit 210B. It should be appreciated that the respective grooves 213A, 213B, 214A, 214B, 218A, 218B, 219A, 219B may be formed with any suitable shape for holding a fixation pin, connecting bar, or other element, such as a fixation wire, according to the selected embodiment of the external fixation system.

Figure 3:
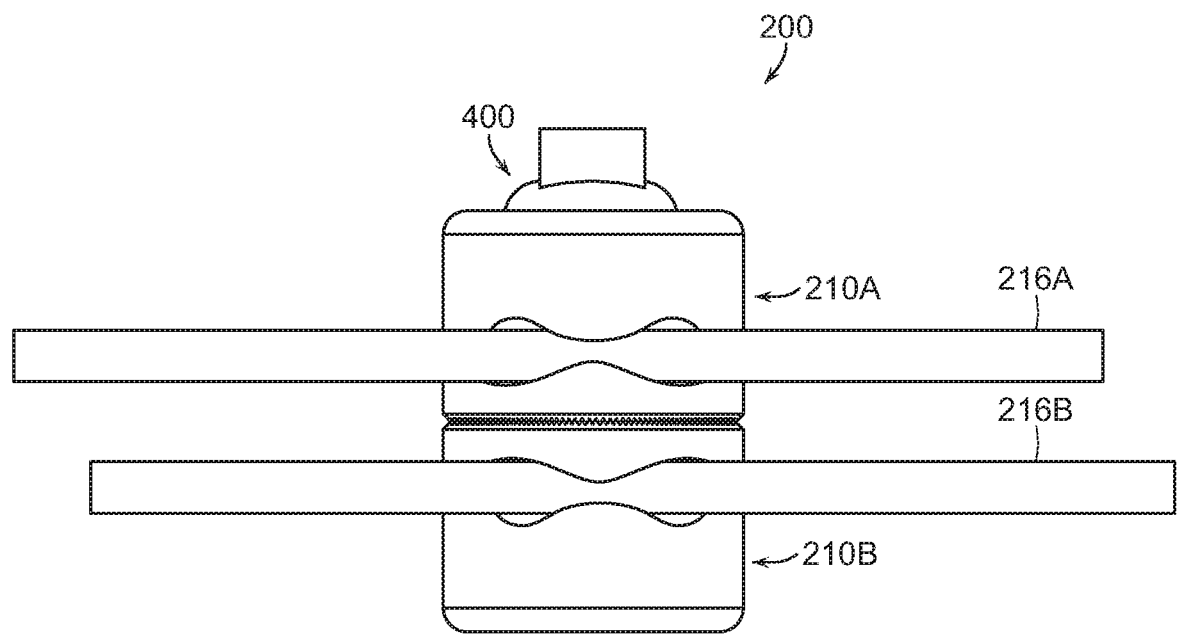
FIG. 3 is a top view of the clamp shown in FIG. 2A.
Figure 4:
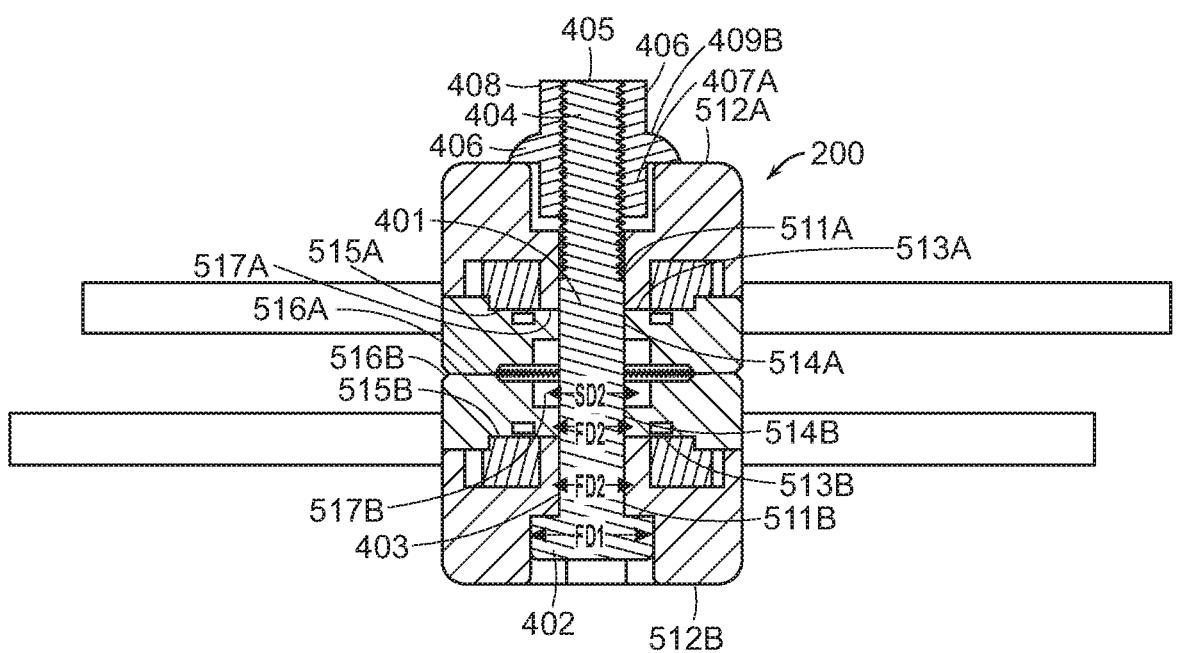
FIG. 4 is a partial cut-away view of the clamp shown in FIGS. 2A and 3.
Figure 14:
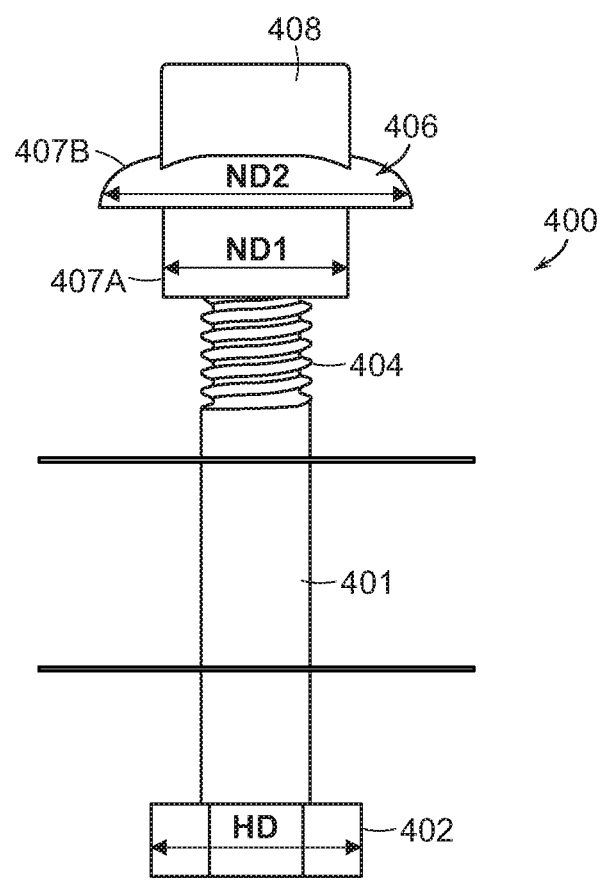
FIG. 14 is a side view of an exemplary embodiment of a compressor.

Referring specifically now to FIGS. 3-4 and 14, it can be seen that the external fixation system 200 may include a compressor 400 to compress the clamp units 210A, 210B together and form the clamp 200. The compressor 400, which is shown in FIG. 14, can include a bolt 401 with a head 402 at one end 403 and threading 404 at an opposite end 405 that threadably engages a shoulder nut 406. The head 402 of the bolt 401 may, in some embodiments, have a hexagonal shape, as is known. The shoulder nut 406 may have a first portion 407A defining a first nut diameter ND1 and a second portion 407B defining a second nut diameter ND2 that is greater than the first nut diameter ND1 so the second portion 407B acts as a flange for the shoulder nut 406. The second portion 407B may also include a torqueing feature 408, shown as a square projection, that can be engaged by an appropriately shaped and sized tool to apply torque to the shoulder nut 406 and displace the shoulder nut 406 along the threading 404 of the bolt 401 to compress the two clamp units 210A, 210B together.

To compress the two clamp units 210A, 210B together, each first component 211A, 211B has a first opening 511A, 511B formed therein that extends from a respective exterior surface 512A, 512B to a respective interior surface 513A, 513B. Similarly, each second component 212A, 212B can have a second opening 514A, 514B formed therein that extends from a respective exterior surface 515A, 515B to a respective interior surface 516A, 516B and at least partially overlaps a respective first opening 511A, 511B to form through-holes 517A, 517B through the clamp 200 in which a portion of the compressor 400, such as the bolt 401, resides. In some embodiments, the first openings 511A, 511B may each define a large first diameter FD1 and a small first diameter FD2 that is smaller than the large first diameter FD1. Similarly, the second openings 514A, 514B may each define a large second diameter SD1 and a small second diameter SD2 that is smaller than the large second diameter SD1. The large first diameter FD1 may be slightly larger than a head diameter HD of the head 402 of the bolt 401 while the small first diameter FD2 is smaller than the head diameter HD so the head 402 may fit within the first opening, such as the first opening 511B. The second portion 407B of the nut 406, on the other hand, may be formed so the second nut diameter ND2 is greater than both the large first diameter FD1 and small first diameter FD2 so the shoulder nut 406 bears on the exterior surface 512A of the first component 211A of the first clamp unit 210A when the compressor 400 compresses the clamp units 210A, 210B together, as will be described further herein.

Figure 14A:
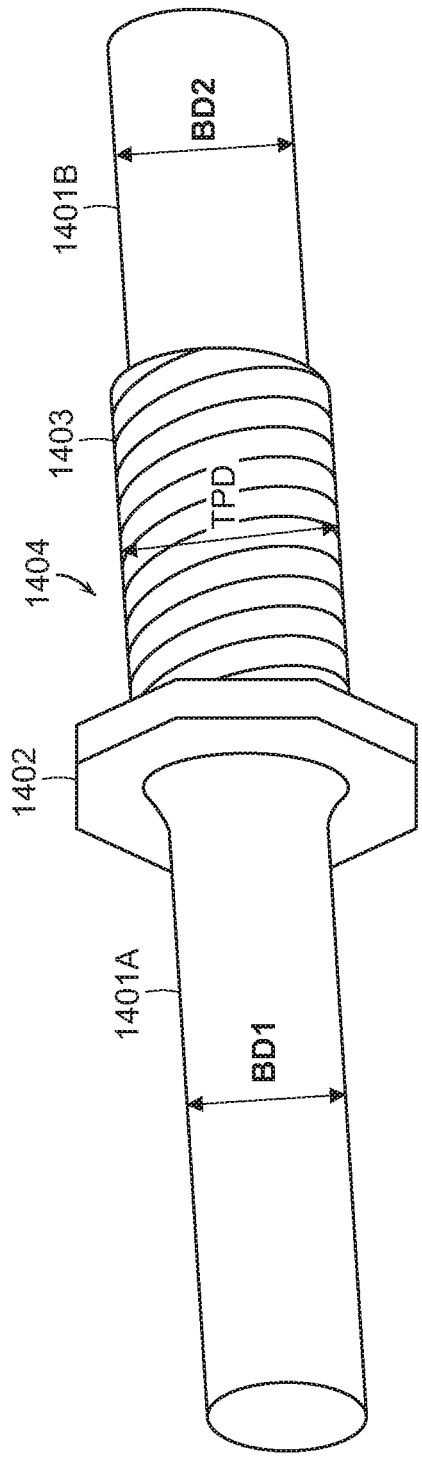
FIG. 14A is a perspective view of an alternative embodiment of a portion of a compressor with bar portions.
Figure 14B:
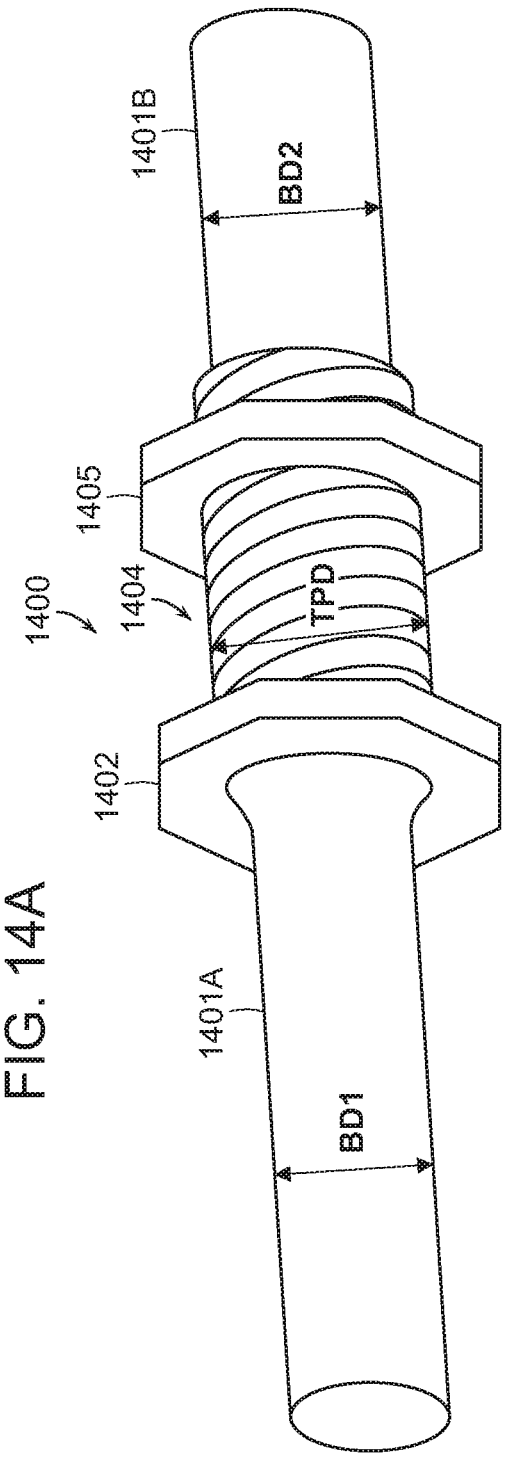
FIG. 14B is a perspective view of the compressor portion shown in FIG. 14A with a nut attached thereto.

Referring now to FIGS. 14A and 14B, an alternative embodiment of a compressor 1400 for compressing clamp units, clamp components, or both together is illustrated that includes one or more bar portions 1401A, 1401B extending therefrom. In some embodiments, one of the bar portions 1401A extends from a head 1402, illustrated as having a hexagonal shape, and the other bar portion 1401B extends from a threaded portion 1403 that connects to the head 1402. While the head 1402 is illustrated as having a hexagonal shape, it should be appreciated that the head 1402 may have other shapes, such as square. The compressor 1400 may define a compressing region 1404 between the head 1402 and threaded portion 1403 that can compress two clamp units together, such as the previously described clamp units 210A and 210B, with a threaded nut 1405 having a complementary threading to the threaded portion 1403.

The bar portion(s) 1401A, 1401B extend from the connecting region 1404 to allow grasping by, for example, additional clamp units, which become interconnected to the clamp units held together by the compressor 1400. In this sense, the compressor 1400 serves the functions of compressing clamp units (or clamp components) together and providing one or more portions 1401A, 1401B to interconnect the compressed clamp units (or clamp components) with other clamp units (or clamp components). In some embodiments, the bar portions 1401A, 1401B define respective bar diameters BD1, BD2, which may be equal to one another, that are between 1 and 15 mm. To allow sliding of the threaded nut 1405 to the threaded portion 1403, the bar diameter BD2 of the bar portion 1401B extending from the threaded portion 1403 may be less than a threaded portion diameter TPD of the threaded portion 1403.

Figure 7:
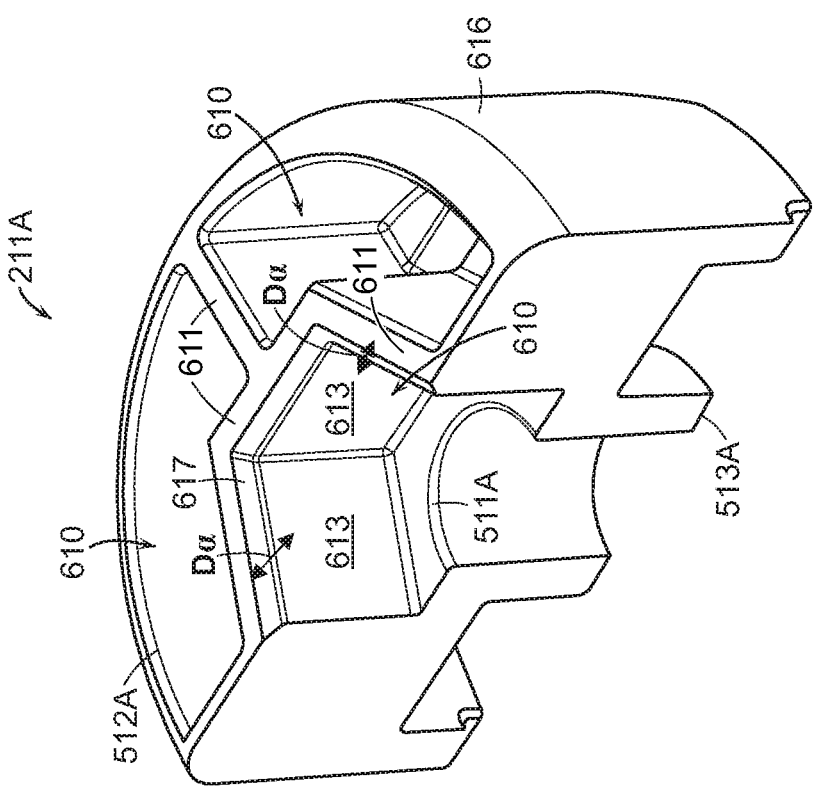
FIG. 7 is a cross-sectional view of the first clamp component shown in FIG. 6 taken along line 7-7.
Figure 6A:
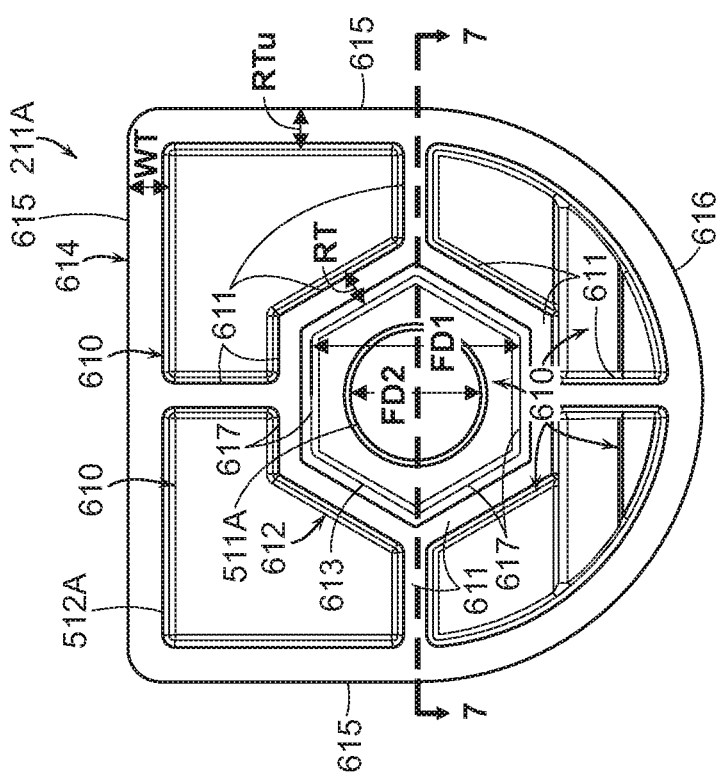
FIG. 6A is a top view of an exterior surface of an exemplary embodiment of a first clamp component.
Figure 6B:
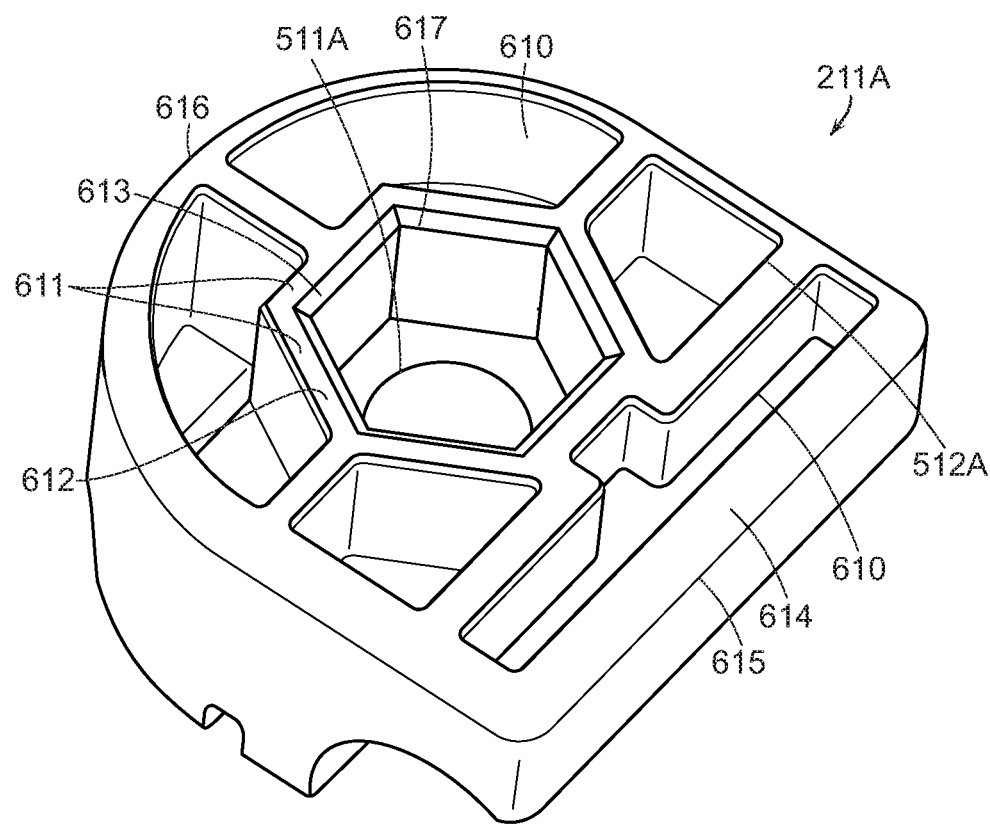
FIG. 6B is a perspective view of the exterior surface shown in FIG. 6A.
Figure 6C:
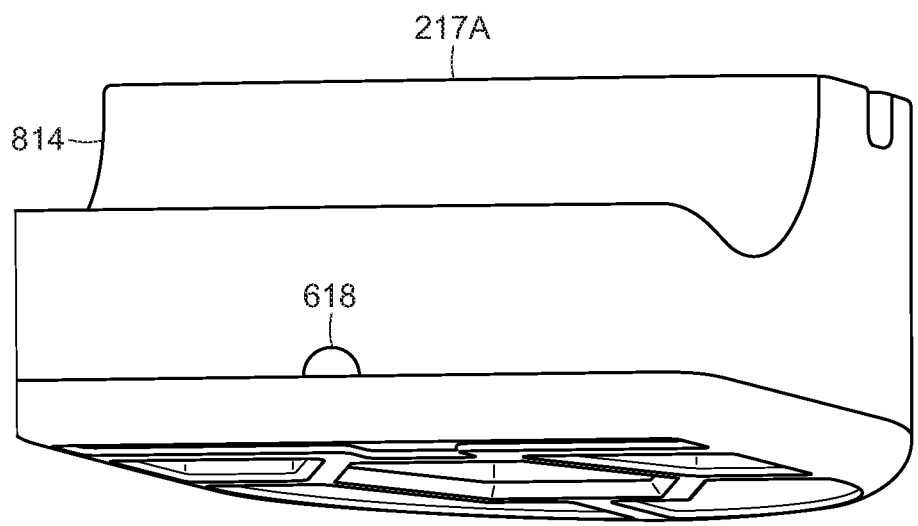
FIG. 6C is another perspective view of the exterior surface shown in FIG. 6A.

Referring now to FIGS. 6A-9, one of the first components 211A is shown alone in greater detail. While the first component 211A is shown in FIGS. 6-9, it should be appreciated that other first components of the external fixation system 200, such as the first component 211B, can be formed similarly or identically to the first component 211A. Referring specifically to FIGS. 6-7, it can be seen that the first component 211A has a plurality of voids 610, shown as seven voids, formed in the exterior surface 512A to define a plurality of interconnected ribs 611. As used herein, a "void" refers to an absence of material formed in the exterior surface 512A but is distinguishable from, for example, an opening, which is formed through both the exterior surface 512A and the opposite interior surface 513A of the first component 211A. The first component 211A comprises a molded metal and, in some embodiments, can consist essentially of the molded metal, which will be described further herein. In some embodiments, the metal at least partially forming the first component 211A is a stainless steel, aluminum, titanium, or other metal with suitable strength and, optionally, may be non-magnetic so the first component 211A may be safely used within a strong magnetic field, such as a magnetic field produced during magnetic resonance imaging (MRI) procedures.

Each of the ribs 611 may define a rib thickness RT between 0.0025 centimeters and 1.5 centimeters, or preferably in a range of between 0.25 centimeters and 1.0 centimeters, depending on the material used to form the ribs 611. As used herein, the "rib thickness" RT refers to a maximum thickness of each rib 611, as one or more of the ribs 611 may have varying thicknesses throughout. In some embodiments some or all of the ribs 611 have a substantially equal rib thickness RT, i.e., each rib 611 may have a rib thickness that deviates from the thickness of some or all of the other ribs by a small enough amount that the ribs 611 are not prone to warping or displacement during the cooling phase of manufacturing, described further herein. It should be appreciated that, when the ribs 611 have a "substantially equal" rib thickness RT, the tolerance for the rib thickness RT may vary based on the material and composition of the liquid composite used for molding, for example. Generally, the rib thickness RT of each of the ribs 611 may, in some embodiments, be of similar uniformity to promote uniform cooling and inhibit the ribs 611 from warping or distorting the adjacent structures supported by the ribs 611.

The ribs 611 may interconnect at a hub 612 that surrounds the first opening 511A of the first component 211A. In some embodiments, the hub 612 can include walls or portions of some of the ribs 611 and define a substantially hexagonal, non-circular, or other suitable shape, which in the illustrated embodiment corresponds to the hexagonal head 402 of the bolt 401, allowing the head 402 to reside within the hub 612 and be rotationally locked with walls 613 of the locking hub 612 such that the head 402 may not rotate. The first component 211A also has a first periphery 614 in which the first pin groove 213A, and optionally the first bar groove 217A, is formed. In some embodiments, the periphery 614 may include one or more linear portions 615 and one or more curved portions 616. In some embodiments, the periphery 614 may be entirely formed of linear portions to define, for example, a square or rectangular cross-section or, alternatively, may be entirely formed of curved portions to define a circular cross-section.

Figure 9:
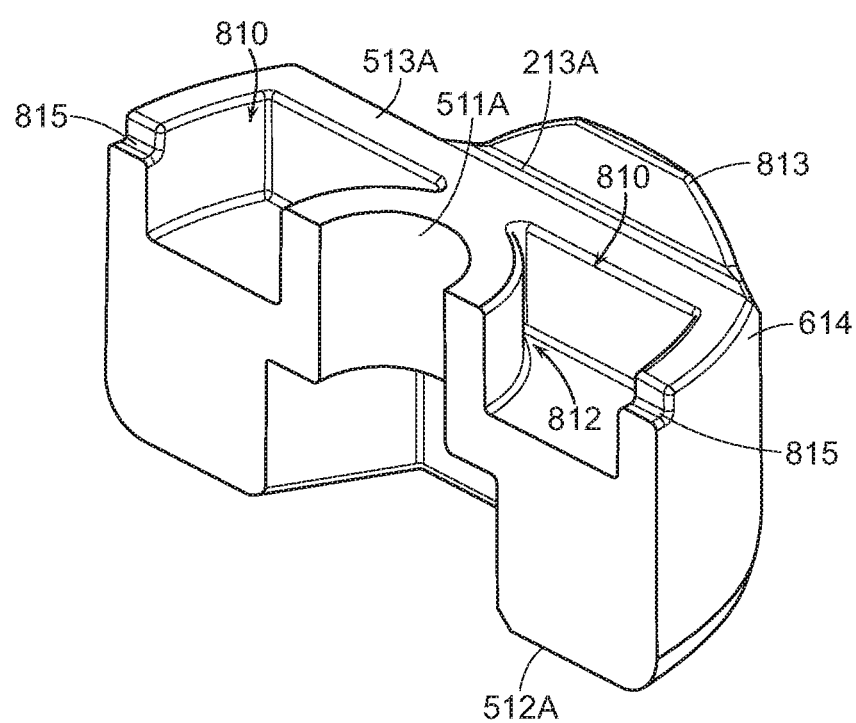
FIG. 9 is a cross-sectional view of the first clamp component shown in FIG. 8A taken along line 9-9.

Referring specifically now to FIGS. 8A-9, the interior surface 513A of the first component 211A is shown in greater detail. As can be seen, the interior surface 513A may also have a plurality of two or more voids 810, shown in this example as two voids, formed therein to define a plurality of interconnected ribs 811. The interconnected ribs 811 each define an interior rib thickness IRT, which in some embodiments may be between 0.0025 centimeters and 1.5 centimeters, or preferably in a range of between 0.25 centimeters and 1.0 centimeters, and/or substantially equal for some or all of the ribs 811. The ribs 811 may interconnect at a hub 812, which may be formed by some of the ribs 811 and define a substantially circular shape surrounding the first opening 511A. Unlike the ribs 611 of the exterior surface 512A, which are all shown as being substantially straight, one or more of the ribs 811 of the interior surface 513A may be formed to have a curved shape in order to produce the circular shape of the hub 812. As previously described, the periphery 614 is formed with at least one first pin groove 213A, which in some embodiments may be at least partially defined by a tab 813 formed in or connected to the periphery 614. Similarly, the periphery 614 may be formed with at least one first bar groove 217A, which in some embodiments may be at least partially defined by another tab 814 formed in or connected to the periphery 614. It should be appreciated that, in some embodiments, the first pin groove(s) 213A and/or the first bar groove(s) 217A may be formed entirely in the material of the periphery 614. The interior surface 513A may also be formed with one or more mating features 815, shown as a pair of mating grooves, that mate with one or more corresponding mating features 1015 (embodiments shown in detail in FIGS. 10-11) of the second component 211B to form an interference fit, properly align the first component 211A and second component 212A relative to one another and inhibit relative rotation between the components 211A, 212A.

In embodiments, first component 211A includes a gate 618 situated on the periphery 614. The gate 618 may be situated on a surface adjacent to the surface containing the plurality of voids 610 and adjacent to tab 814. In some embodiments, the gate 618 is shaped as a semicircle but may be formed as any curved or angular shape. In further embodiments, the flat edge of the semicircular gate 618 lies adjacent to the surface of first component 211A containing the plurality of voids 610. The gate 618 may be trimmed flush to a surface of the first component 211A prior to sintering to remove any burrs or gate vestige.

Figure 10:
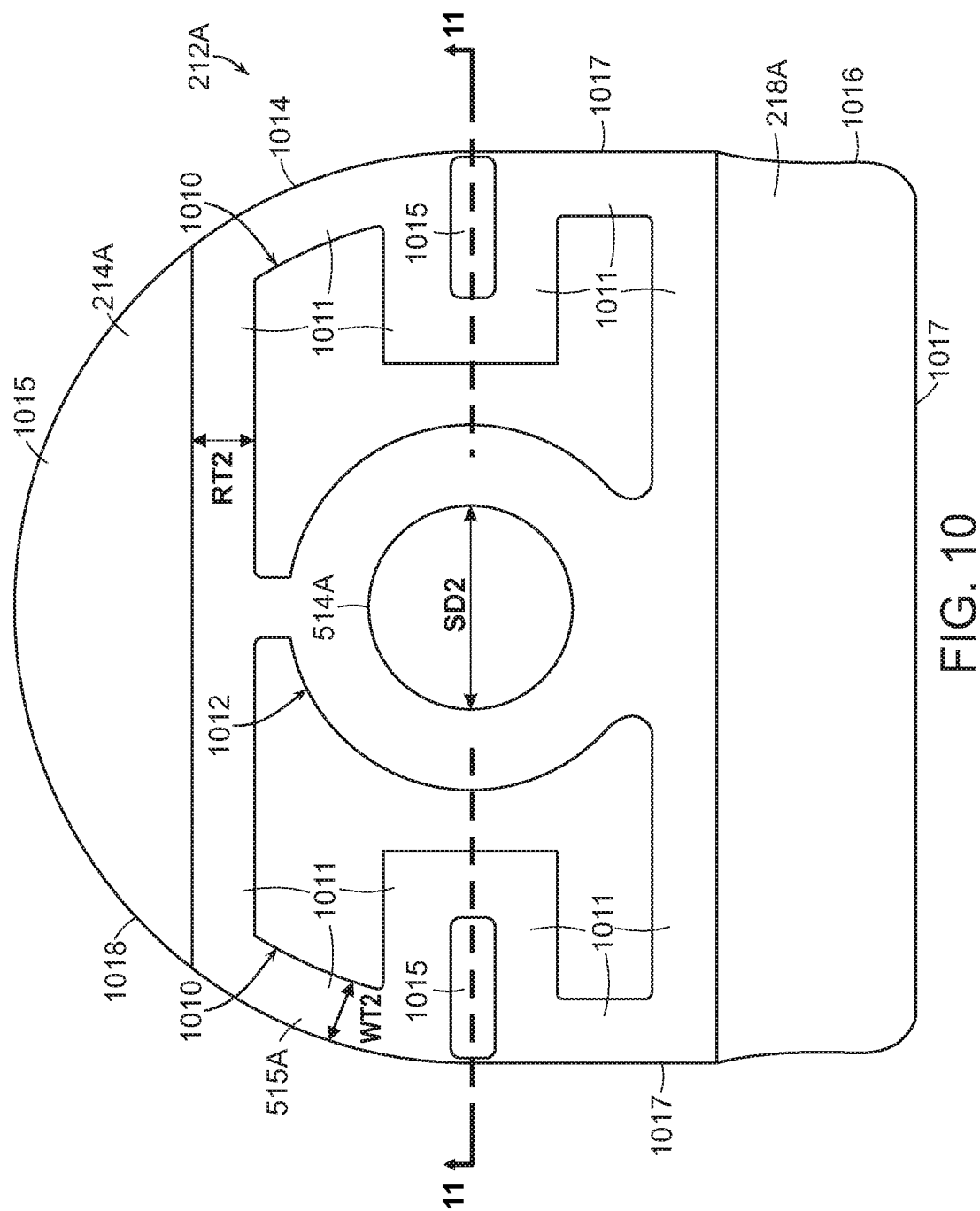
FIG. 10 is a top view of an exterior surface of an exemplary embodiment of a second clamp component.
Figure 11:
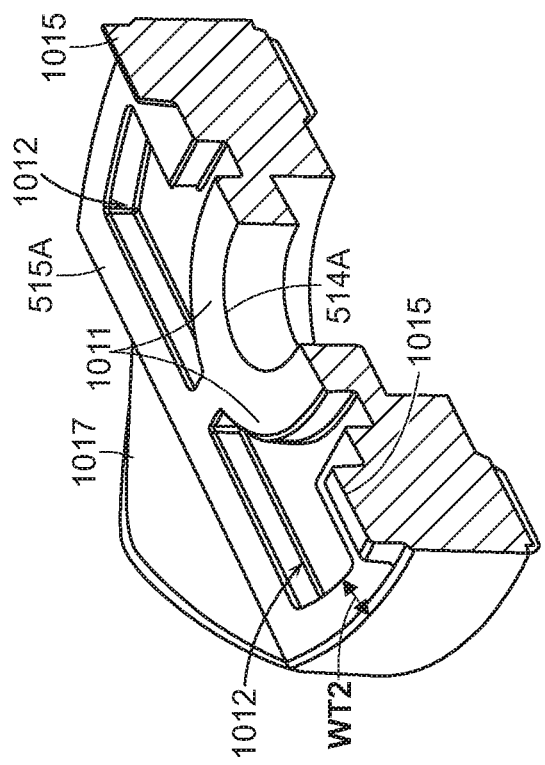
FIG. 11 is a cross-sectional view of the second clamp component shown in FIG. 10 taken along line 11-11.

Referring now to FIGS. 10-13, one of the second components 212A is shown alone in greater detail. While the second component 212A is shown in FIGS. 10-13, it should be appreciated that other second components of the external fixation system 200, such as the second component 212B, can be formed similarly or identically to the second component 212A. Referring specifically now to FIGS. 10-11, it can be seen that the second component 212A has a plurality of voids 1010, shown as two voids, formed in the exterior surface 515A to define a plurality of interconnected ribs 1011, similarly to the first component 211A. In some embodiments, the second component 212A also comprises a molded metal, and may consist of the molded metal, which will be described further herein. It should be appreciated that, in some embodiments, the second component 212A can be formed with the exterior surface 515A having similar features to the exterior surface 512A of the first component 211A. Each of the ribs 1011 defines a rib thickness RT2, which in some embodiments may be between 0.001 inches and 0.6 inches and/or substantially equal for some or all of the ribs 1011. The ribs 1011 may interconnect at a hub 1012, which in some embodiments includes some of the ribs 1011 and has a substantially circular shape surrounding the second opening 514A formed through the second component 211A. The one or more second pin grooves 214A formed in a second periphery 1014 of the second component 211A may be at least partially defined by a tab 1015 formed in or otherwise connected to the second periphery 1014.

Similarly, the one or more second bar grooves 218A may be formed in the second periphery 1014 of the second component 211A and may be at least partially defined by another tab 1016 formed in or otherwise connected to the second periphery 1014. In some embodiments, the second periphery 1014 may include one or more linear portions 1017 connected to one another and one or more curved portions 1018, similarly to the first periphery 614 of the first component 211A. In some embodiments, the second periphery 1014 may be entirely formed of linear portions to define, for example, a rectangular or square cross-section or, alternatively, in some embodiments the second periphery 1014 may be entirely formed of curved portions to define, for example, a circular cross-section.

Figure 13:
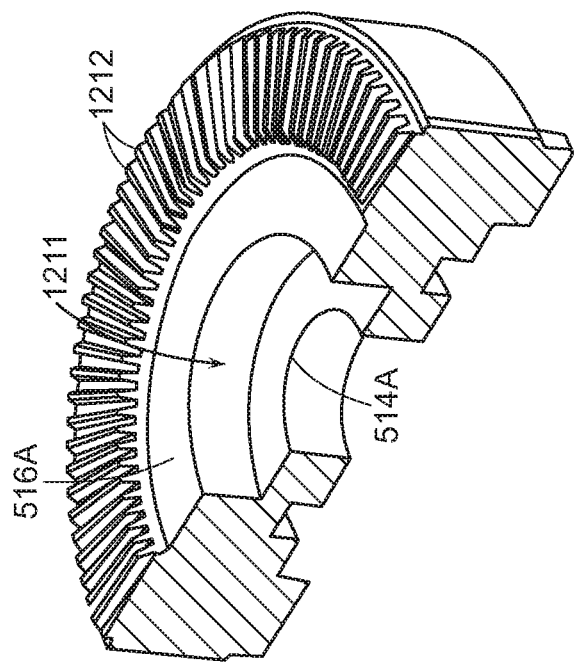
FIG. 13 is a cross-sectional view of the second clamp component shown in FIG. 12 taken along line 13-13.
Figure 12A:
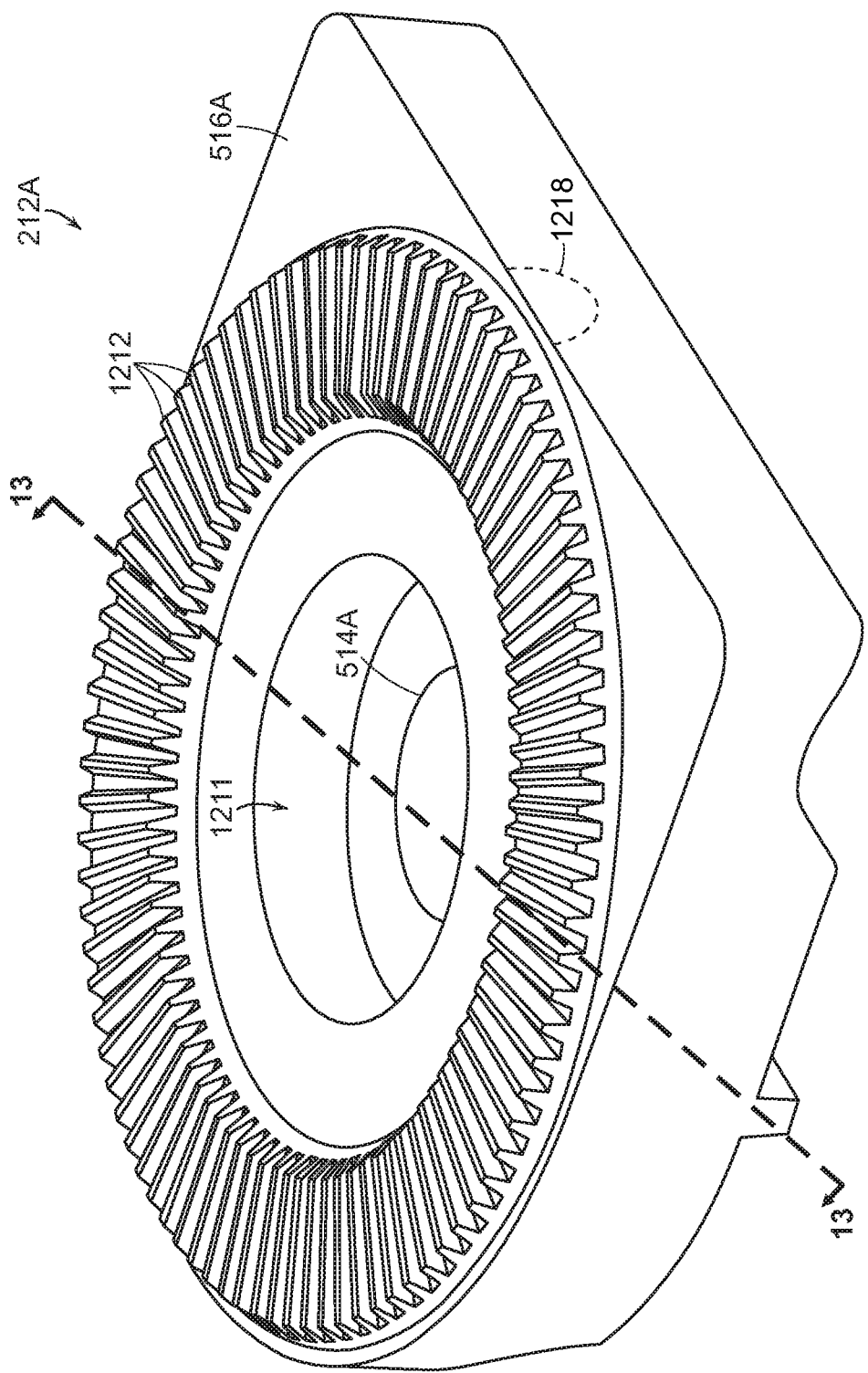
FIG. 12A is a perspective view of an interior surface of the second clamp component shown in FIGS. 10-11.
Figure 12B:
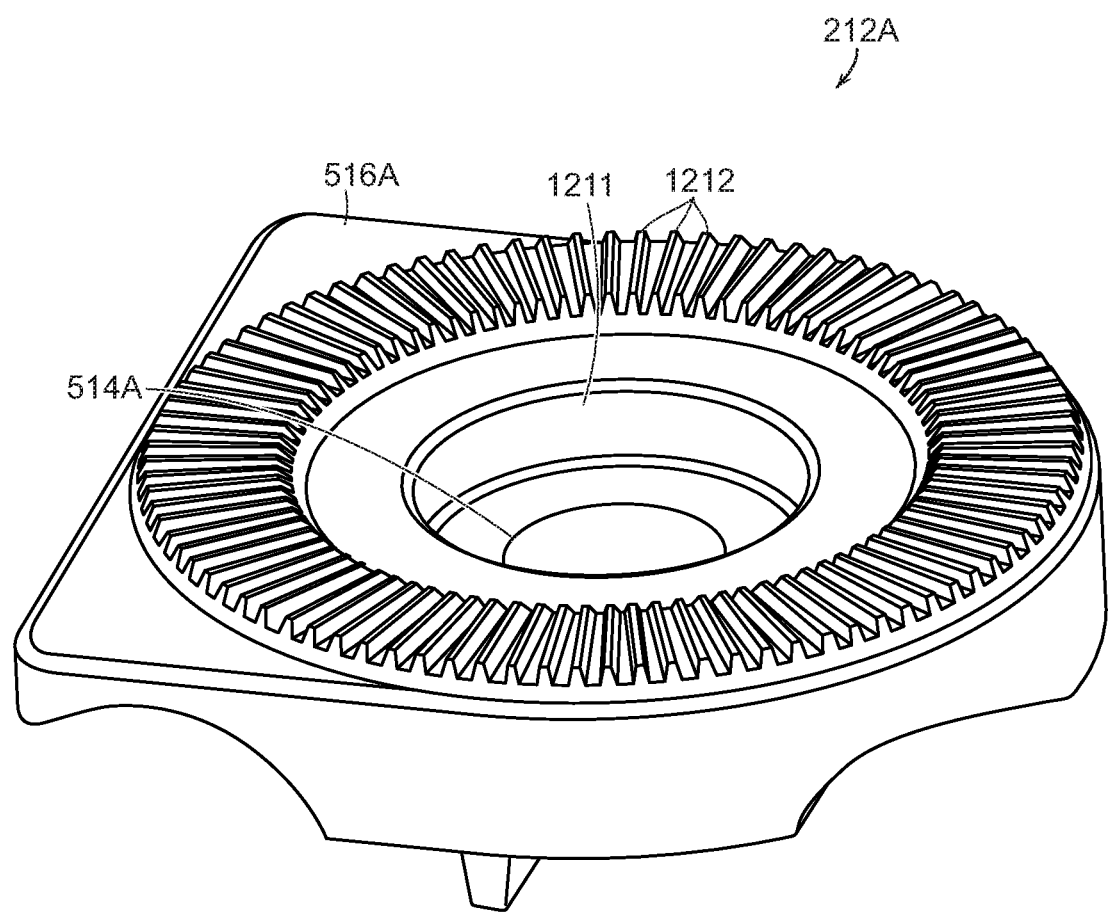
FIG. 12B is another perspective view of an interior surface of the second clamp component shown in FIGS. 10-11.

Referring specifically now to FIGS. 12-13, the interior surface 516A of the second component 212A is shown in greater detail. The interior surface 516A can be formed with a single void 1211 defining an entryway to the second opening 514A formed through the second component 212A. The void 1211 also provides a cavity to place a spring or other element to separate adjacent second components 212A, 212B from each other by a gap when the clamp 200 is not tightened. A spring may also force the second components 212A, 212B against their respective first components 211A, 211B prior to tightening so the clamp units 210A, 210B can hold bars and pins in place prior to final tightening and so the respective mating features 815, 1015 mate to prevent relative rotation between the first components 211A, 211B and second components 212A, 212B. In some embodiments, the interior surface 516A is formed with a plurality of locking features 1212, shown as teeth, to rotationally lock the two clamp units 210A, 210B together by intermeshing or mating the locking features 1212 of two second components 212A, 212B together. The locking features 1212 may be arranged, for example, as a ring of teeth 1212 surrounding the void 1211 and second opening 514A. The number of teeth 1212, spacing between adjacent teeth 1212, and other features of the teeth 1212 may be adjusted, as desired, to achieve the desired interlocking between two second components 212A, 212B.

In some embodiments, second component 212A includes a gate 1218 situated on the periphery 614. The gate 618 may be situated on a surface adjacent to the surface containing the plurality of teeth 1212 and adjacent to tab 1214. In some embodiments, the gate 1218 is shaped as a semicircle but may be formed as any curved or angular shape. In further embodiments, the flat edge of the semicircular gate 1218 lies adjacent to the surface of second component 212A containing the plurality of teeth 1212. The gate 1218 may be trimmed flush to a surface of the first component 212A prior to sintering to remove any burrs or gate vestige.

Referring again to FIGS. 2A and 3-4, it can be seen how the two clamp units 210A, 210B each having a respective first component 211A, 211B and respective second component 212A, 212B can be compressed together by the compressor 400 to form the clamp 200. The clamp 200 may be formed by abutting the interior surfaces 513A, 513B of the first components 511A, 511B against the exterior surfaces 515A, 515B of a respective second component 512A, 512B, with the respective mating features 815, 1015 of each component 511A, 511B, 512A, 512B assisting in properly orienting the components 511A, 512A, 511B, 512B relative to one another. Before, or once, the clamp units 210A, 210B are formed, fixation pins 216A, 216B may be placed in respective fixation pin holders 215A, 215B and/or connecting bars 220A, 220B may be placed in respective bar holders 219A, 219B. The interior surfaces 516A, 516B of the second components 212A, 212B are placed together such that the locking features 1212 intermesh with another and the clamp units 210A, 210B abut against each other in the proper orientation. The bolt 401 of the compressor 400 may then be placed in the formed through-holes 517A, 517B and the shoulder nut 406 torqued so the shoulder nut 406 bears on the ribs 611 of, for example, the first component 211A while the bolt head 402 bears on the surface surrounding the first opening 511B of the first component 211B to compress the clamp units 210A, 210B together to form the clamp 200, simultaneously compressing the fixation pins 216A, 216B and connecting bars 220A, 220B held by the clamp units 210A, 210B. Due to the ribs 611 being interconnected and having rib thicknesses RT that are perpendicular to the compression load of the compressor 400, the compressive load applied to the ribs 611 is evenly distributed across the ribs 611 so the first component 211A has sufficient strength to withstand the compressive load. To reduce the risk of the compressive load being concentrated in one particular component, the exterior surfaces 512A, 512B, 515A, 515B and interior surfaces 513A, 513B, 516A, 516B can all be substantially parallel to one another, i.e., flat, so the compressive load is evenly distributed across surfaces bearing on one another. Once the shoulder nut 406 is sufficiently torqued to produce the desired compressive load to stably hold the fixation pins 216A, 216B and connecting bars 220A, 220B, the clamp 200 may be connected to other clamps of the external fixation system 100 via the connecting bars 220A, 220B.

Referring now to FIGS. 2B-2G, yet another exemplary embodiment of a clamp unit 210D is illustrated that includes a pair of identical clamp components 290 compressed together to hold one or more fixation elements 281, such as pins, wires, and bars. The clamp components 290 may be compressed together by, for example, a pair of compressors, such as the previously described compressor 400.

Figure 2B:
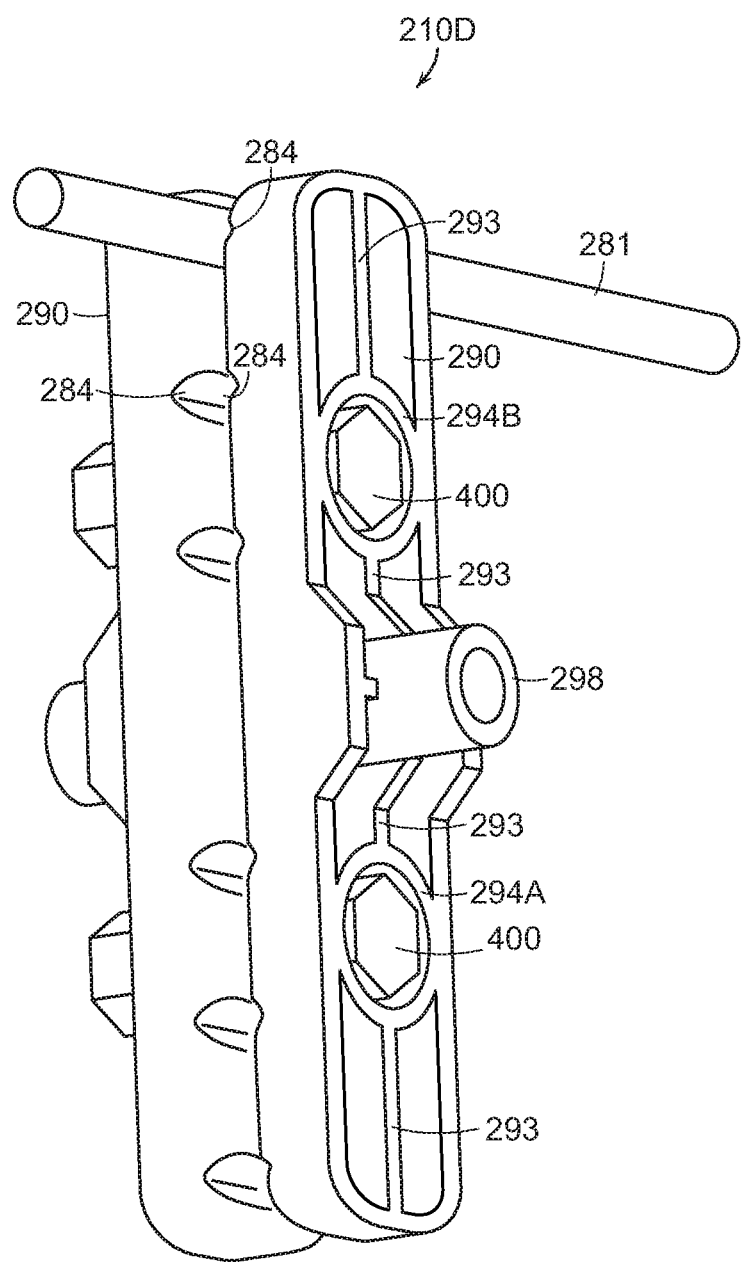
FIG. 2B is a perspective view of another exemplary embodiment of a clamp unit including identical clamp components connected to one another.
Figure 2C:
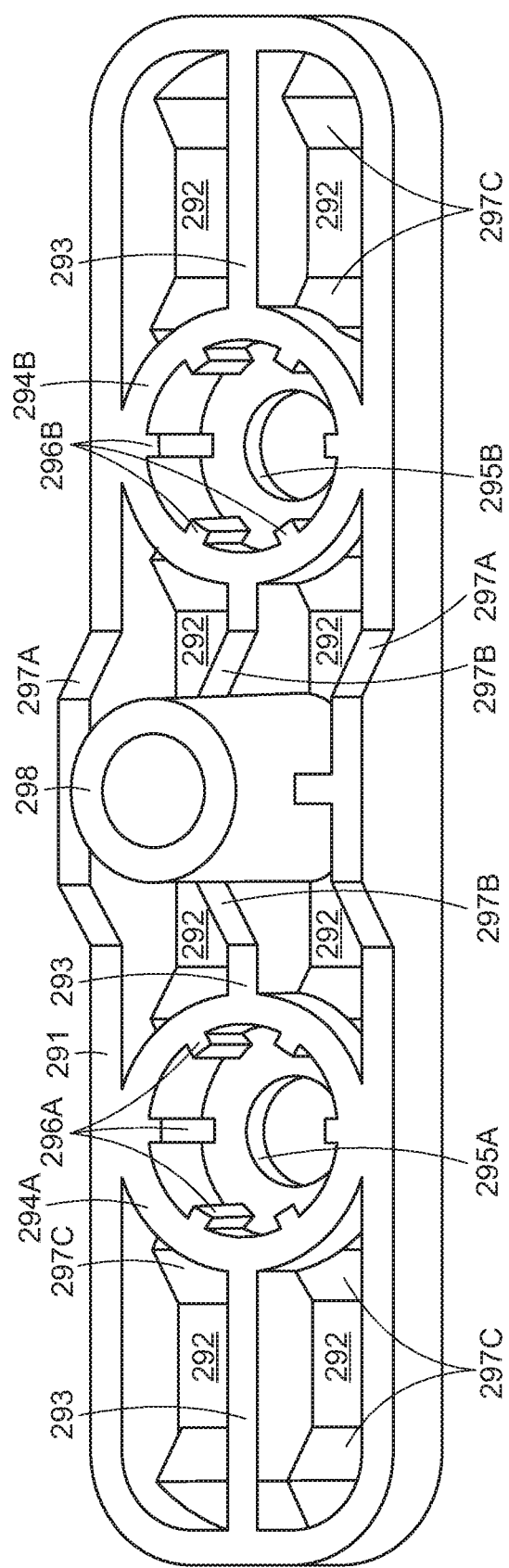
FIG. 2C is a perspective view of an exterior surface of one of the clamp components illustrated in FIG. 2B.
Figure 2F:
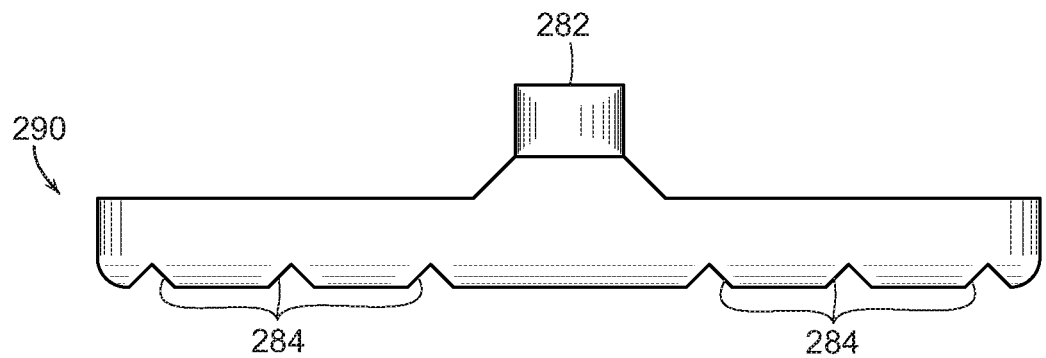
FIG. 2F is a side view of one of the clamp components illustrated in FIG. 2B.
Figure 2G:
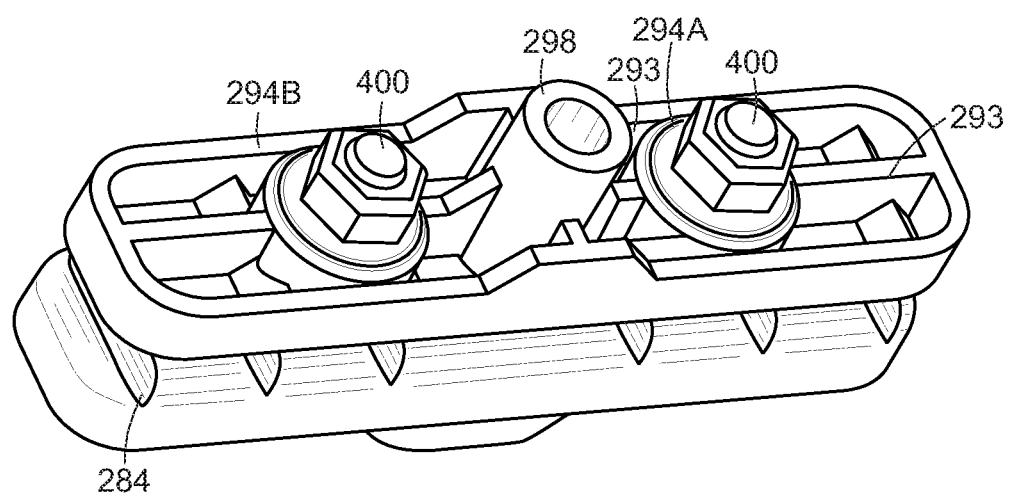
FIG. 2G is a perspective view of the clamp unit as shown in FIG. 2B.

Referring specifically now to FIGS. 2C and 2D, an exterior surface 291 of the clamp components 290 is illustrated and includes a plurality of voids 292 formed therein to define a plurality of interconnected ribs 293. In some embodiments, one or more of the ribs 293 can be connected to one another at one or more hubs 294A, 294B, which may be circular and surround a respective opening 295A, 295B. The openings 295A, 295B may be aligned with corresponding openings 295A, 295B of another clamp component 290 to form through-holes that hold the compressors 400. In some embodiments, the hubs 294A, 294B each include respective grasping projections 296A, 296B to limit the ability of the compressors 400 to rotate when placed through the through-holes. In some embodiments, the clamp components 290 can have multiple sets of hubs 294A, 294B and corresponding openings 295A, 295B. As a non-limiting example, the claim component depicted in FIG. 16A includes 2 sets of hub and corresponding openings.

In some embodiments, the exterior surface 291 is formed with a plurality of ramped portions 297A, 297B, 297C, which may be formed at different depths and regions in the exterior surface 291. The ramped portions 297A, 297B, 297C can encourage easy removal of the clamp components 290 from a mold during manufacturing, which is described further herein. In some embodiments, the ramped portions 297A, which may be formed adjacent to edges of the exterior surface 291, can act as spacers, which will be described further herein.

In some embodiments, the exterior surface 291 also includes a mounting structure 298 extending therefrom that allows mounting of, for example, additional clamp components or clamp units to the clamp component 290. The mounting structure 298 may have, for example, a hollow cylindrical shape extending away from the exterior surface 291 and defining a mounting opening 282 formed through to an interior surface 283 of the clamp component 290 that can accept a compressing element. It should be appreciated that, in some embodiments, the mounting structure 298 may have a solid shape that is similar to a fixation element, such as a fixation bar. The mounting structure 298 promotes interconnection of the clamp component 290 to other clamp units or clamp components, which may be spaced from the exterior surface 291 by the ramped portion 297A.

Referring specifically now to FIG. 2E, the interior surface 283 of the clamp component 290 is illustrated. The interior surface 283 has one or more pin grooves 284, shown as six pin grooves 284, formed therein that extend to a periphery 285 of the clamp component 290. While the clamp component 290 is illustrated with six pin grooves 284, it should be appreciated that the clamp component 290 may include fewer than six pin grooves 284, e.g., one, two, or three pin grooves 294, or more than six pin grooves 284, e.g., seven, eight, nine, or ten pin grooves 284. When two clamp components 290 are compressed together with their respective pin groove(s) 284 aligned with the pin groove(s) 284 of the other clamp component 290, the aligned pin grooves 284 can hold a fixation element, such as the fixation element 281 illustrated in FIG. 2E. As illustrated, the periphery 285 of the clamp component 290 may include linear portions connected at the corners by curved portions so the clamp component 290 has a generally rectangular cross-section with rounded, rather than right angle, corners. In some embodiments, the periphery 285 is formed with right angle corners so the clamp component 290 has a substantially rectangular cross-section.

In other respects, the clamp components 290 can have similar features to the previously described clamps components 211A, 211B, 212A, 212B. It should therefore be appreciated how the clamp components 290 can be used as modular components to form the clamp unit 210D.

From the foregoing, it should be appreciated that the clamp 200 may be formed by modular components 211A, 211B, 212A, 212B, 290 that can be easily assembled into clamp units 210A, 210B, 210D for forming the clamp 200. In some embodiments, each clamp unit 210A, 210B, 210D may individually be used as a clamp for fixating pins and forming an external fixation system by connecting to other clamp units using connecting bars, with a modified connector 400 having a shorter bolt 401 holding the respective components 211A, 212A, 211B, 212B, 290 of the clamp units 210A, 210B, 210D together to form such a clamp. In this respect, each clamp unit 210A, 210B, 210D may individually function as a clamp or be combined with other clamp units to form a clamp for use in an external fixation system.

Figure 15:
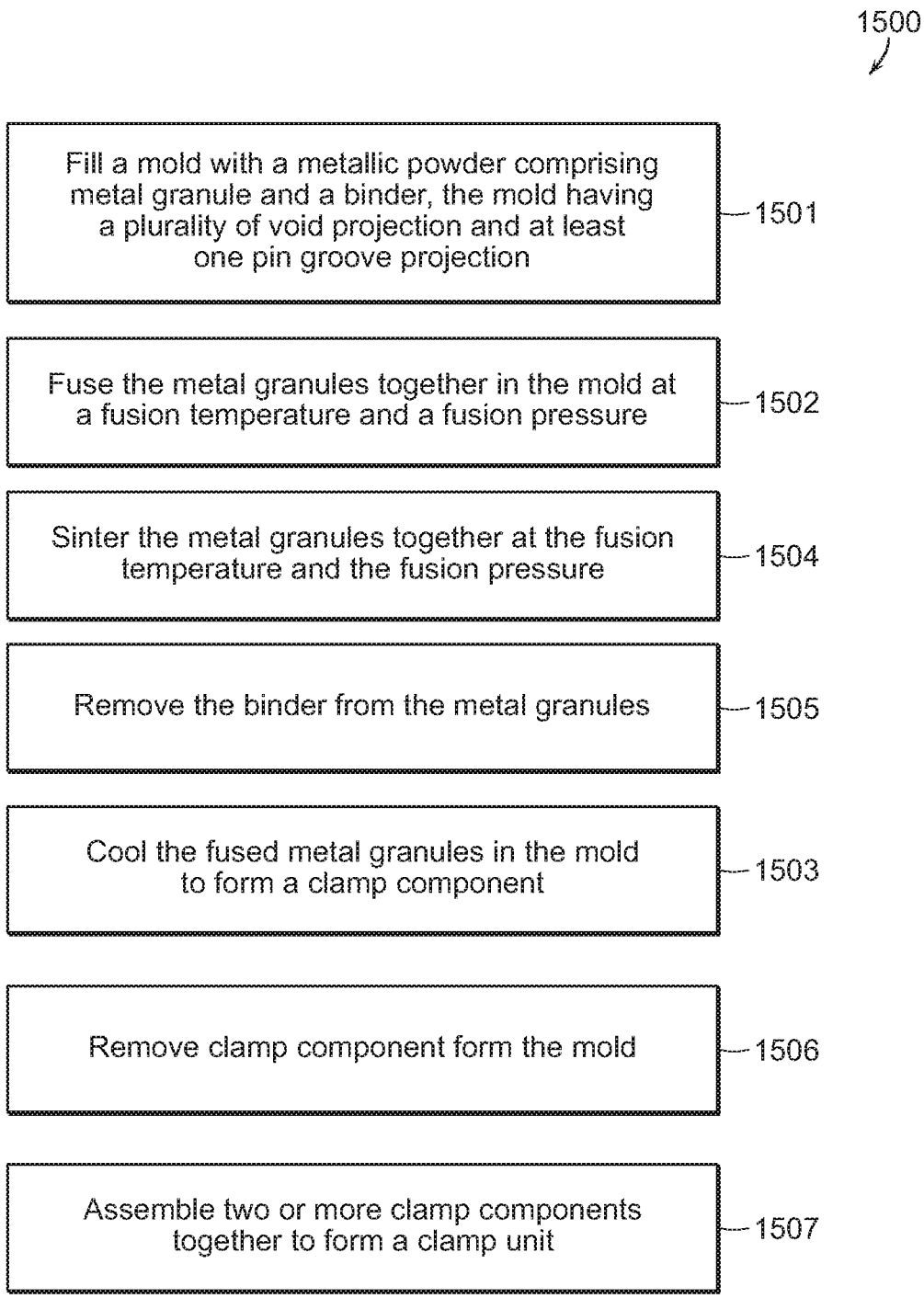
FIG. 15 is a flow chart illustrating an exemplary embodiment of a method of forming a clamp component.

Referring now to FIG. 15, an exemplary embodiment of a method 1500 of forming a clamp component, such as the first component 211A, 211B, second component 212A, 212B, or clamp component 290 is shown. It should be appreciated that embodiments of the method 1500 include one or more techniques of "metal injection molding." Exemplary metal injection molding techniques are generally described by U.S. Patent Application Publication No. 2007/0178005 to Broadley et al., which is incorporated by reference in its entirety herein. The method 1500 includes filling 1501 a mold with a metallic powder comprising metal granules, which will be the metal(s) that ultimately form the produced component. It should be appreciated that the mold does not need to be completely filled with the metallic powder to form the clamp component. In some embodiments, the metallic powder includes metal granules of one or more metals, such as iron and nickel, and a binder material, such as wax. The metal granules may have average particle sizes of 20 µm or less. The mold has a plurality of void projections to form corresponding voids in the component, such as voids 610, and define a plurality of corresponding interconnected ribs in the component, such as ribs 611, and at least one pin groove projection to form one or more corresponding pin grooves in the component, such as the first pin groove 213A. In some embodiments, the mold may be formed as two or more sub-molds that are held together in order to form the mold. The metal granules are fused 1502 together in the mold to form the clamp component, such as the first component 211A.

The fusing 1502 may comprise heating the metal granules to a fusion temperature and a fusion pressure so the metal granules fuse together to form a substantially solid material. The fusion temperature depends on what metal(s) is included in the metallic powder, but can be at least 500° C., for example. In some embodiments, the fusion temperature and the fusion temperature are chosen so the metal granules are sintered 1504 together. In some embodiments, the binder material in the metallic powder evaporates or is otherwise removed 1505 from the metal granules during or after the fusing 1502 so the formed component substantially consists of the metal granules, i.e., the final formed component comprises less than 2% binder material and consists substantially of the molded metal. Optionally, the fused metal granules may be cooled 1503 in the mold before the formed component is removed 1506 from the mold. In some embodiments, the formed component is removed 1506 from the mold while still at, or close to, the fusion temperature and cooled 1503 outside of the mold. Once two or more components are formed and removed from the mold, the components can be assembled 1507 together to form a clamp unit, as previously described.

Figure 16A:
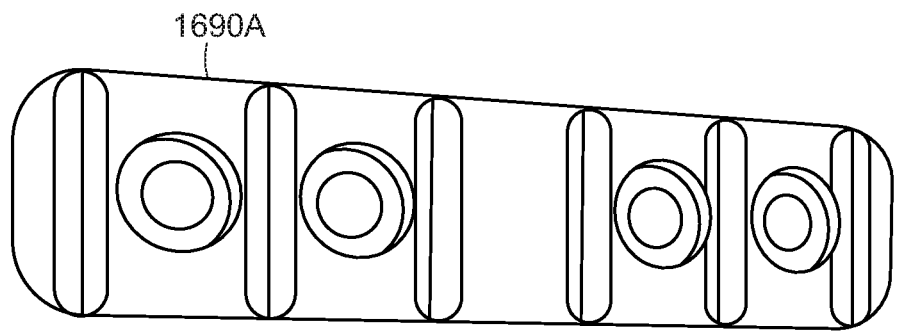
FIG. 16A is top view of a clamp component before and after sintering.
Figure 16A:
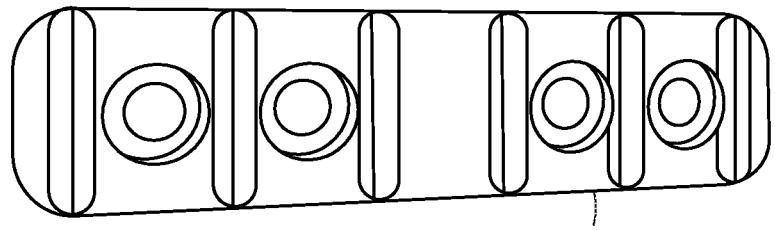
Figure 16B:
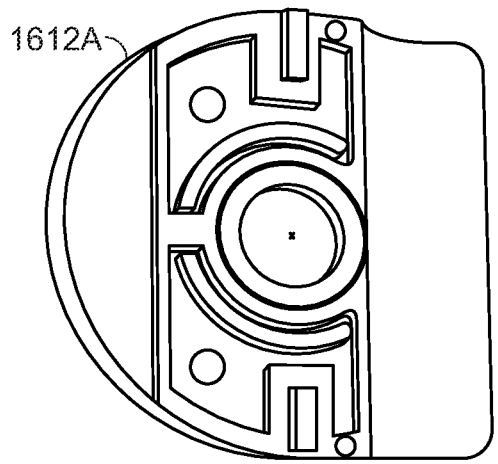
FIG. 16B is top view of first and second clamp components before and after sintering.
Figure 16B:
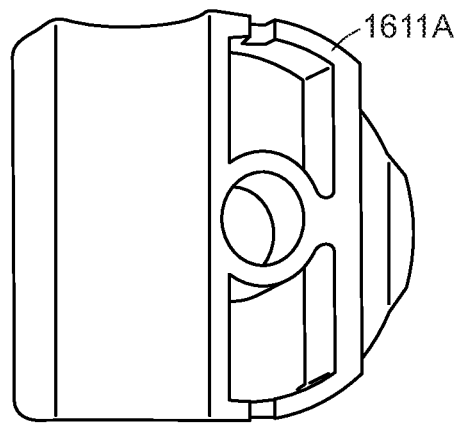
Figure 16B:
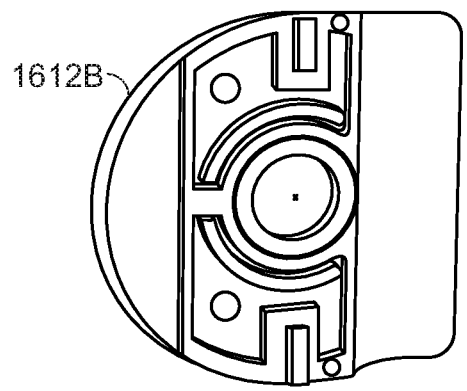
Figure 16B:
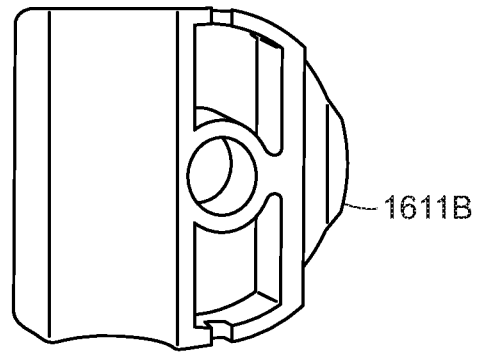

Referring to FIGS. 16A and 16B, components produced before and after sintering 1504 are shown. "Green" parts 1690A, 1611A, and 1612A are components formed before sintering. Finished parts 1690B, 1611B, and 1612B are components formed after sintering. As can be seen from FIGS. 16A and 16B, sintering reduces the size of a component by a range of 10-15%. In some embodiments, size reduction can be 10%, 11%, 12%, 13%, 14%, 15%, or any percentage therebetween.

To assist with molding, and referring again to FIGS. 6-7, the void projections of the mold may be formed with draft edges so some or all of the formed interconnected ribs, such as ribs 611, have an edge 617 defining a draft angle Dα relative to the exterior surface 512A. In some embodiments, the draft angles Dα are between 0.5° and 1.5°, but it should be appreciated that the draft angles Dα may be other values as well. The draft angles Dα can allow the formed components to be molded in a single pull mold. In some embodiments, the parting lines for the mold are oriented perpendicular to a central axis of the formed part to reduce or eliminate the need for secondary polishing procedures to address potential imperfections caused by a witness line. Further, molding the inner and outer surfaces of the formed components as flat, planar surfaces can facilitate fusing 1502 the metal granules, which may comprise sintering, to reduce or eliminate the need for additional fixtures for sintering.

In some embodiments, the formed component, such as first component 211A, has wall thicknesses WT (shown in FIGS. 6 and 8) that are similar to the rib thicknesses RT of the ribs 611 and interior rib thicknesses IRT of the ribs 811. Additionally, the second component 212A can be molded to have second wall thicknesses WT2 (shown in FIGS. 10-11) that are similar to the wall thicknesses WT of the first component 211A. Forming the first component 211A with wall thicknesses WT that are similar to the rib thicknesses RT, IRT of the ribs 611, 811 and second wall thicknesses WT2 of the second component 212A allows for molding of the first component 211A and second component 212A using one family mold, reducing the need for multiple family molds and associated cost.

Figure 17A:
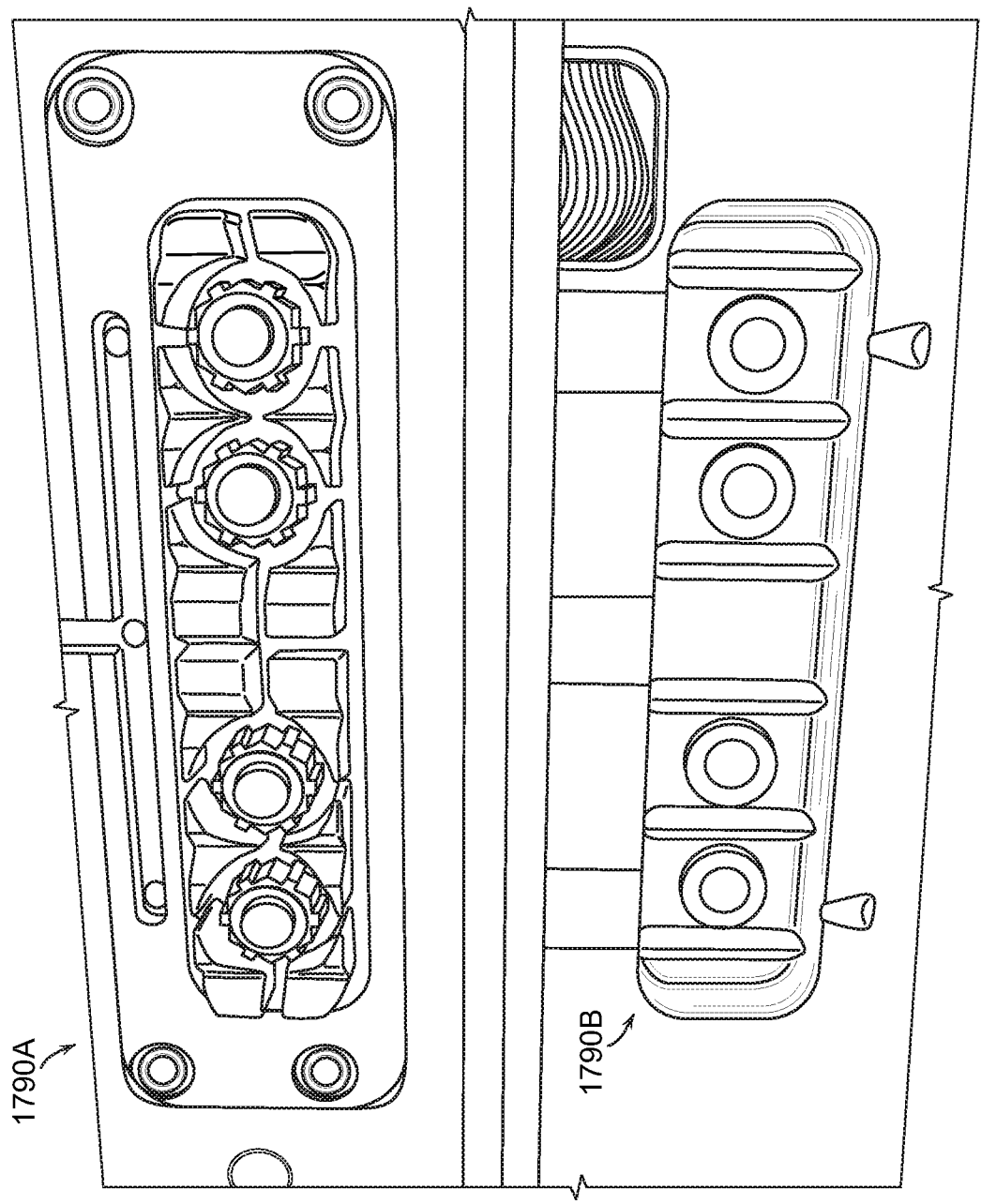
FIG. 17A is a top view of a mold for creating a clamp component.

Referring to FIGS. 17A and 17B, exemplary depictions of family molds are shown. In some embodiments, a mold includes first sub-mold 1790A and a second sub-mold 1790B. Sub-molds 1790A and 1790B may be joined together and filled with a metallic powder through a port as described above to create a clamp component. Another family mold includes sub-molds 1711A and 1711B, which may be joined together and filled with a metallic powder as described above to create first component 211. Another mold includes sub-molds 1712A and 1712B, which may be joined together and filled with a metallic powder as described above to create second component 212.

From the foregoing, it should be appreciated that the method 1500 disclosed herein provides an efficient method to rapidly produce clamps, such as clamp 200, for use in an external fixation system without machining of the components. Molding the clamp components 211A, 211B, 212A, 212B from metallic powder can be performed relatively quickly and inexpensively compared to known methods, which often require post-formation processing and machining to finally produce the part, while avoiding issues associated with using plastic materials, which often experience material creep and do not generally have the same strength as similar metal components. Rapid manufacturing of the clamps allows, for example, a manufacturer to rapidly fill orders from stock material without having to stockpile produced clamps in order to meet customer demand. Molding the clamp components 211A, 211B, 212A, 212B can also reduce the amount of material used to form the clamp 200, reducing the cost and weight of the parts as well as reducing waste that may be generated during, for example, machining. In some embodiments, forming voids in the clamp components may reduce the volume of material needed to form a clamp component, such as clamp component 211A, by between 30% and 70%, such as between 40% and 50%, relative to a comparable component that is solid and does not include voids. Utilizing computer assisted drawing (CAD) software to form the clamp molds can also allow efficient scaling up or down of the final clamp size and the ability to produce many differently sized, similarly shaped clamps from a common baseline clamp mold design.

In some embodiments, a kit includes various disconnected clamp components, such as clamp components 211A, 211B, 212A, 212B, to assemble the clamp components 211A, 211B, 212A, 212B into the clamp units 210A, 210B and assemble the external fixation system 200. Two or more of the clamp components 211A, 211B, 212A, 212B may be provided in a package, which may also include assembly instructions for assembling a clamp unit from the disconnected clamp components, as part of the kit. It should therefore be appreciated that the clamp units 210A, 210B may be provided in an assembled or dissembled state to form the external fixation system 200.

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims set forth below.

What is claimed is:

1. An external fixation system for a medical procedure, comprising:
   at least one pair of clamp components that form a clamp unit, the at least one pair of clamp components including:
      a first clamp component comprising a molded metal, the first molded metal clamp component including a first surface having a first plurality of voids formed therein and a first plurality of molded metal interconnected ribs, that extend across the first surface to a molded metal first periphery extending around at least one first connector opening formed through a portion of the first molded metal clamp component, the at least one first connector opening defined by a molded metal hub rib wherein the voids are defined by interior surfaces of the molded metal interconnected ribs, exterior surfaces of the molded metal hub rib and the molded metal first periphery; and
      a second clamp component comprising the molded metal, the second molded metal clamp component configured to be mated with the first clamp molded metal component, the second molded metal clamp component having a second surface with a second plurality of voids and a second plurality of molded metal interconnected ribs that extend across the second surface to a second molded metal periphery extending around at least one second connector opening formed through a portion of the second molded metal clamp component, the at least second connector opening defined by a second molded metal hub rib wherein the second plurality of voids are defined by interior surfaces of the second plurality of molded metal interconnected ribs, an exterior surface of the molded metal hub rib and the second molded metal periphery, the first molded metal clamp component having at least one first connector groove and the second molded metal clamp component having at least one second connector groove that aligns with the at least one first connector groove to form a clamp unit fixation element holder such that the clamp unit is configured to connect to a second clamp unit to form the external fixation system.

2. The external fixation system of claim 1, wherein the at least one first connector groove and the at least one second connector groove comprise a first bar groove and a second bar groove, respectively, that together form at least one of a plurality of bar holders, the external fixation system further comprising a connecting bar held within at least one of the bar holders.

3. The external fixation system of claim 1 wherein the at least one pair of molded metal clamp components further comprises a first pair of molded metal clamp components connected to a second identical pair of molded metal clamp components with a compressor.

4. The external fixation system of claim 3, wherein the first pair of molded metal clamp components and the second pair of molded metal clamp components are rotationally locked with one another via at least one locking feature formed with a surface of at least one molded metal clamp component.

5. The external fixation system of claim 4, wherein the at least one locking feature comprises a plurality of interlocking teeth.

6. The external fixation system of claim 1, wherein the clamp unit is connected to the second clamp unit by a connecting bar.

7. The external fixation system of claim 1, wherein each of the molded metal interconnected ribs defines a rib thickness between 0.0025 centimeters and 1.5 centimeters.

8. The external fixation system of claim 7, wherein at least one of the plurality of molded metal interconnected ribs has a curved shape.

9. The external fixation system of claim 1, wherein each of the plurality of molded metal interconnected ribs are interconnected to one another by the hub rib surrounding the first connector opening.

10. The external fixation system of claim 9, wherein the hub rib includes some of the plurality of molded metal interconnected ribs to define a hexagonal shape.

11. The external fixation system of claim 9, wherein the hub rib defines a circular shape.

12. The external fixation system of claim 1, wherein each of the plurality of molded metal interconnected ribs each define a substantially equal rib thickness.

13. The external fixation system of claim 1, wherein the second connector opening extends through a second interior surface to a second exterior surface opposite the second interior surface of the second clamp component and at least partially overlaps the first connector opening of the first clamp component to form a through-hole, the external fixation system further comprising a compressor having a portion placed in the connector opening of each clamp component and is configured to compress the molded metal clamp components together.

14. The external fixation system of claim 13, wherein the compressor comprises a portion bearing on the plurality of molded metal interconnected ribs of the first molded metal clamp component of the clamp unit.

15. The external fixation system of claim 1, wherein at least some of the plurality of ribs have an edge defining a draft angle of between 0.5° and 1.5°.

16. The external fixation system of claim 1, wherein at least one of the first molded metal clamp component and the second molded metal clamp component comprises a non-magnetic metal.

17. The external fixation system of claim 1, wherein at least one of the first periphery and the second periphery defines at least one linear portion and at least one curved portion.

18. The external fixation system of claim 1, wherein the second periphery has at least one tab that at least partially defines at least one pin opening.

19. The external fixation system of claim 1, further comprising a fixation pin held in the at least one fixation element holder.

20. The external fixation system of claim 1, wherein at least one molded metal clamp component has at least 3 voids.

21. The external fixation system of claim 1, wherein at least one molded metal clamp component has at least 4 voids and at least two openings to receive two clamp connectors.

22. The external fixation system of claim 1, further comprising a third molded metal clamp component having teeth.

23. The external fixation system of claim 22, further comprising a fourth molded metal clamp component.

24. A method of using the system of claim 1 wherein a plurality of clamp units including at least one clamp unit including the first molded metal clamp component and the second molded metal clamp component of claim 1 are connected by at least one bar, and at least one pin is connected to an orthopedic member of a patient.

25. An external fixation system for a medical procedure, comprising:
at least one pair of clamp components that form a clamp unit, the at least one pair of clamp components including:
a first clamp component comprising a molded metal, the first clamp molded metal component including a first surface having a first plurality of voids formed therein and a first plurality of molded metal interconnected ribs that extend across the first surface to a molded metal first periphery extending around at least one first connector opening formed through a portion of the first molded metal clamp component, the at least one first connector opening defined by a molded metal hub rib wherein the voids are defined by interior surfaces of the molded metal interconnected ribs, exterior surfaces of the molded metal hub rib and the molded metal first periphery, at least one interior surface having a draft angle; and
a second clamp component comprising the molded metal, the second molded metal clamp component configured to be mated with the first clamp molded metal component, the second molded metal clamp component having a second surface with a second plurality of voids and a second plurality of molded metal interconnected ribs that extend across the second surface to a second molded metal periphery extending around at least one second connector opening formed through a portion of the second molded metal clamp component, the at least second connector opening defined by a second molded metal hub rib wherein the second plurality of voids are defined by interior surfaces of the second plurality of molded metal interconnected ribs, an exterior surface of the molded metal hub rib and the second molded metal periphery, the first molded metal clamp component having at least one first connector groove and the second molded metal clamp component having at least one second connector groove that aligns with the at least one first connector groove to form a clamp unit fixation element holder such that the clamp unit is configured to connect to a second clamp unit to form the external fixation system.

26. The external fixation system of claim 25, wherein the at least one first connector groove and the at least one second connector groove comprise a first bar groove and a second bar groove, respectively, that together form at least one of a plurality of bar holders, the external fixation system further comprising a connecting bar held within at least one of the bar holders.

27. The external fixation system of claim 25 wherein the at least one pair of molded metal clamp components further comprises a first pair of molded metal clamp components connected to a second identical pair of molded metal clamp components with a compressor.

28. The external fixation system of claim 27, wherein the first pair of molded metal clamp components and the second pair of molded metal clamp components are rotationally locked with one another via at least one locking feature formed with a surface of at least one molded metal clamp component.

29. The external fixation system of claim 28, wherein the at least one locking feature comprises a plurality of interlocking teeth.

30. The external fixation system of claim 25, wherein the clamp unit is connected to the second clamp unit by a connecting bar.

31. The external fixation system of claim 25, wherein each of the molded metal interconnected ribs defines a rib thickness between 0.0025 centimeters and 1.5 centimeters.

32. The external fixation system of claim 25, wherein each of the plurality of molded metal interconnected ribs are interconnected to one another by the molded metal rib hub.

33. The external fixation system of claim 25, wherein the molded metal rib hub includes some of the plurality of molded metal interconnected ribs to define a hexagonal shape.

34. The external fixation system of claim 25, wherein at least one of the plurality of molded metal interconnected ribs has a curved shape.

35. The external fixation system of claim 25, wherein the molded metal rib hub defines a circular shape.

36. The external fixation system of claim 25, wherein each of the plurality of molded metal interconnected ribs each define a substantially equal rib thickness.

37. The external fixation system of claim 25, wherein the second connector opening extends through a second interior surface to a second exterior surface opposite the second interior surface of the second molded metal clamp component and at least partially overlaps the first connector opening of the first molded metal clamp component to form a through-hole, the external fixation system further comprising a compressor having a portion placed in the connector opening of each molded metal clamp component and is configured to compress the molded metal clamp components together.

38. The external fixation system of claim 37, wherein the compressor comprises a portion bearing on the plurality of molded metal interconnected ribs of the first molded metal clamp component of the clamp unit.

39. The external fixation system of claim 25, wherein at least some of the plurality of molded metal ribs have an edge defining the draft angle that is between 0.5° and 1.5°.

* * * * *